(12) United States Patent
Brittain et al.

(10) Patent No.: US 8,609,863 B2
(45) Date of Patent: *Dec. 17, 2013

(54) BENDAMUSTINE PHARMACEUTICAL COMPOSITIONS

(71) Applicant: Cephalon, Inc., Frazer, PA (US)

(72) Inventors: Jason Edward Brittain, El Cajon, CA (US); Joe Craig Franklin, Tulsa, OK (US)

(73) Assignee: Cephalon, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/719,379

(22) Filed: Dec. 19, 2012

(65) Prior Publication Data

US 2013/0123316 A1 May 16, 2013

Related U.S. Application Data

(63) Continuation of application No. 13/654,898, filed on Oct. 18, 2012, now Pat. No. 8,461,350, which is a continuation of application No. 11/330,868, filed on Jan. 12, 2006, now Pat. No. 8,436,190.

(60) Provisional application No. 60/644,354, filed on Jan. 14, 2005.

(51) Int. Cl.
C07D 235/04 (2006.01)

(52) U.S. Cl.
USPC .......................... 548/304.7; 34/284

(58) Field of Classification Search
USPC .......................... 34/284; 548/304.7
See application file for complete search history.

(56) References Cited

U.S. PATENT DOCUMENTS

| | | |
|---|---|---|
| 3,590,028 A | 6/1971 | Report et al. |
| 4,012,448 A | 3/1977 | Smith et al. |
| 4,537,883 A | 8/1985 | Alexander et al. |
| 4,659,699 A | 4/1987 | Francis |
| 4,670,262 A | 6/1987 | Battelli et al. |
| 5,066,647 A | 11/1991 | Palepu et al. |
| 5,130,305 A | 7/1992 | Palepu et al. |
| 5,183,746 A | 2/1993 | Shaked et al. |
| 5,192,743 A | 3/1993 | Hsu et al. |
| 5,204,335 A | 4/1993 | Sauerbier et al. |
| 5,227,373 A | 7/1993 | Alexander et al. |
| 5,227,374 A | 7/1993 | Alexander et al. |
| 5,268,368 A | 12/1993 | Palepu |
| 5,413,995 A | 5/1995 | Alexander et al. |
| 5,418,223 A | 5/1995 | Palepu et al. |
| 5,750,131 A | 5/1998 | Wichert et al. |
| 5,770,230 A | 6/1998 | Teagarden et al. |
| 5,776,456 A | 7/1998 | Anderson et al. |
| 5,955,504 A | 9/1999 | Wechter et al. |
| 5,972,912 A | 10/1999 | Marek et al. |
| 6,034,256 A | 3/2000 | Carter et al. |
| 6,077,850 A | 6/2000 | Carter et al. |
| 6,090,365 A | 7/2000 | Kaminski et al. |
| 6,271,253 B1 | 8/2001 | Carter et al. |
| 6,380,210 B1 | 4/2002 | Desimone et al. |
| 6,492,390 B2 | 12/2002 | Carter et al. |
| 6,545,034 B1 | 4/2003 | Carson et al. |
| 6,569,402 B1 | 5/2003 | Cheesman et al. |
| 6,573,292 B1 | 6/2003 | Nardella |
| 6,613,927 B1 | 9/2003 | Kwok |
| 8,436,190 B2 | 5/2013 | Brittain et al. |
| 2002/0102215 A1 | 8/2002 | Klaveness et al. |
| 2003/0232874 A1 | 12/2003 | Nardella |
| 2004/0053972 A1 | 3/2004 | Nara |
| 2004/0058956 A1 | 3/2004 | Akiyama et al. |
| 2004/0072889 A1 | 4/2004 | Masferrer |
| 2004/0096436 A1 | 5/2004 | Carson et al. |
| 2004/0152672 A1 | 8/2004 | Carson et al. |
| 2004/0247600 A1 | 12/2004 | Leoni |
| 2005/0020615 A1 | 1/2005 | Rubino |
| 2005/0060028 A1 | 3/2005 | Horres et al. |
| 2005/0176678 A1 | 8/2005 | Horres et al. |
| 2006/0051412 A1 | 3/2006 | Petereit et al. |
| 2006/0128777 A1 | 6/2006 | Bendall et al. |
| 2009/0264488 A1 | 10/2009 | Cooper et al. |
| 2011/0190363 A1 | 8/2011 | Drager et al. |
| 2012/0071532 A1 | 3/2012 | Cooper et al. |
| 2013/0041003 A1 | 2/2013 | Brittain et al. |

FOREIGN PATENT DOCUMENTS

| | | |
|---|---|---|
| DE | 34727 | 12/1964 |
| DE | 80967 | 6/1970 |
| DE | 159289 | * 6/1981 |
| DE | 159289 | 3/1983 |
| DE | 159877 | 4/1983 |
| DE | 293808 | 9/1991 |
| DE | 10016077 | 12/2001 |
| DE | 10306724 | 9/2003 |
| DE | 10304403 | 8/2004 |
| EP | 0656211 | 6/1995 |

(Continued)

OTHER PUBLICATIONS

Kanekal et al., Kanekal et al. (SDX-105(TREANDA) Enhances the Tumor Growth Inhibitory Effect of Rituximab in Daudi Lymphoma Xenografts, 2004, Blood (ASH Annual Meeting Abstracts), vol. 104.*

RxList, Treanda, 2013, pp. 1-2.*

Ni et al, Use of pure t-butanol as a solvent for freeze-drying: a case study, 2001, International Journal of Pharmaceitcs, vol. 2001, pp. 39-46.*

(Continued)

*Primary Examiner* — Ali Soroush

(74) *Attorney, Agent, or Firm* — Woodcock Washburn LLP

(57) ABSTRACT

The present invention provides pharmaceutical formulations of lyophilized bendamustine suitable for pharmaceutical use. The present invention further provides methods of producing lyophilized bendamustine. The pharmaceutical formulations can be used for any disease that is sensitive to treatment with bendamustine, such as neoplastic diseases.

4 Claims, 6 Drawing Sheets

(56) References Cited

FOREIGN PATENT DOCUMENTS

| EP | 0780386 | 6/1997 |
|---|---|---|
| EP | 1354952 | 10/2003 |
| EP | 1444989 | 8/2004 |
| WO | WO 96/28148 | 9/1996 |
| WO | WO 97/08174 | 3/1997 |
| WO | WO 03/066027 | 8/2003 |
| WO | WO 03/081238 | 10/2003 |
| WO | WO 03/086470 | 10/2003 |
| WO | WO 03/094990 | 11/2003 |
| WO | WO 2006/076620 | 7/2006 |
| WO | WO 2009/120386 | 10/2009 |

OTHER PUBLICATIONS

Aivado et al., "Bendamustine in the treatment of chronic lymphocytic leukemia: Results and future perspectives", Seminars in Oncology, Aug. 2002, 29(4), 19-22, Suppl. 13.
Barman Balfour et al., "Bendamustine", Drugs, 2001, 61(5), 631-638, Auckland, New Zealand.
Berge et al., "Pharmaceutical Salts", Journal of pharmaceutical sciences, Jan. 1977, 66(1), 1-19.
Bremer, Karl, "High rates of long-lasting remissions after 5-day bendamustine chemotherapy cycles in pre-treated low-grade non-hodgkin's-lymphomas", Journal of Cancer Research and Clinical Oncology, 2002, 128(11), 603-609.
Byrn et al., "Pharmaceutical Solids: A Strategic Approach to Regulatory Consideration", Pharmaceutical Research, Jul. 1995, 12(7), 945-954.
Chow et al., "Anti-CD20 antibody (IDEC-C2B8, rituximab) enhances efficacy of cytotoxic drugs on neoplastic lymphocytes in vitro: role of cytokines complement, and caspases", Haematologica, Jan. 2002, 87(1), 33-43.
Chow et al., "In AML Cell Lines Ara-C Combined with Purine Analogues is Able to Exert Synergistic as Well as Antagonistic Effects on Proliferation, Apoptosis and Disruption of Mitochondrial Membrane Potential", Leukemia & Lymphoma, 2003, 44(1), 165-173.
Chow et al., "In vitro induction of apoptosis of neoplastic cells in low-grade non-Hodkin's lymphomas by combinations of established cytotoxic drugs with bendamustine", Haematologica, May 2001, 86(5), 485-493.
Chow et al., "Synergistic effects of chemotherapeutic drugs in lymphoma cells are associated with down-regulation of inhibitor of apoptosis proteins (IAPs), prostate-apoptosis-response-gene 4(Par-4), death-associated protein (Dazz) and with enforced caspase activation", Biochemical Pharmacology, Jan. 2003, 66(5), 711-724.
Department of Health and Human Services, Food and Drug Administration, "International Conference on Harmonisation; Guidance on Impurities: Residual Solvents," Federal Register, Dec. 24, 1997, 62(247), 67377-67388.
Diehl et al., "Bendamustine in the Treatment of Hematologic Malignancies", Semin. Oncol., Aug. 2002, 29(4), 1-3, Suppl. 13, Saundes, Philadelphia, PA.
EC Safety Data Sheet: Ribomustin® in http://www.docstoc.com/docs/22323231/EC-Safety-Data-Sheet-Bendamustin (published: Jul. 3, 1998; updated Mar. 1, 2007), 8 pages.
Fichtner et al., "Antineoplastic activity and toxicity of some alkylating cytostatics (cyclophosphamide, CCNU, cytostasan) encapsulated in liposomes in different murine tumor models", Journal of Microencapsulation, Jan. 1986, 3(2), 77-87.
Gandhi, Varsha, "Metabolism and mechanisms of action of bendamustine: Rationales for combination therapies", Seminars in Oncology, Aug. 2002, 29(4), 4-11, Suppl. 13.
Goodman et al., The Pharmacological Basis of Therapeutics, 1985, 7th edition, Macmillan publishing company, New York.
Gust et al., "Investigations on the Stability of Bendamustin, a Cytostatic Agent of the Nitrogen Mustard Type, I. Synthesis, Isolation, and Characterization of Reference Substances", Monatshefte fur Chemie, 1997, 128(3), 291-299.

Heider et al., "Efficacy and toxicity of bendamustine in patients with relapsed low-grade non-Hodgkin's lymphomas", Anti-Cancer Drugs, 2001, 12(9), 725-729.
Kath et al., "Bendamustine monotherapy in advanced and refractory chronic lymphocytic leukemia", Journal of Cancer Research and Clinical Oncology, 2001, 127(1), 48-54.
Koenigsman et al., "Fludarabine and Bendamustine in Refractory and Relapsed Indolent Lymphoma a Multicenter Phase IIII Trial of the East German Society of Hematology and Oncology (OSHO)", Leukemia & Lymphoma, 2004, 45(9), 1821-1827.
Kollmannsberger et al., "Phase II study of bendamustine in patients with relapsed or cisplatin-refractory germ cell cancer", Anti-Cancer Drugs, 2000, 11(17), 535-539.
Konstantinov et al., Cytotoxic efficacy of bendamustine in human leukemia and breast cancer eel/lines, Journal of Cancer Research and Clinical Oncology, 2002, 128(5), 271-278.
Köster et al., "Carboplatin in combination with bendamustine in previously untreated patients with extensive-stage small lung cancer (SCLC)", Clinical Drug Investigation, 2004, 24(10), 611-618.
Leoni et al., "Sdx-105 (Trenda), Active in Non-Hodgkins Lymphoma Cells, Induces the Mitotic Catastrophe Death Pathway", Blood, 104(11), 2004, Abs 4593, p. 232b.
Maas, "Stabilitat von Benamustinhydrochlorid in Infusionslosungen", Pharmazie, 1994, 49(10), 775-777 (Translation Included).
McKim et al., "Dimethyl Sulfoxide USP, PhEur in Approved Pharmaceutical Products and Medical Devices," Pharmaceutical Technology, May 2, 2008, 1-7.
Mottu et al., "Organic solvents for pharmaceutical parenterals and embolic liquids: A review of toxicity data," PDA J. Pharma. Sci. & Tech. 54(6) Nov.-Dec. 2000, 456-469.
Ni et al., "Use of pure t-butanol as a solvent for freeze-drying: a case study", International Journal of Pharmaceutics, Sep. 2001, 226(1-2), 39-46.
Niemeyer et al., "SDX-105 (bendamustine) is a clinically active chemotherapeutic agent with a distinct mechanism of action", Proc Annu Meet Am Assoc Cancer Res, Mar. 2004, 45, 1st ed., 2 pages.
Nowak et al., "Upon Drug-Induced Apoptosis in Lymphoma Cells X—linked Inhibitor of Apoptosis (XIAP) Translocates from the Cytosol to the Nucleus", Leukemia & Lymphoma, Jul. 2004, 45(7), 1429-1436.
Ozegowski et al., "IMET 3393, gamma-(1-methyl-5-bis-(β-chloräthyl)-amino-benzimidazolyl(2)-buttersäure-hydrochlorid, ein neues Zytostatikum aus der Reihe der Benzimidazol-Loste", Zbl Pharm., 1971;110, Heft 10, 1013-1019 (Translation Included).
Ponisch et al., "Bendamustine in the treatment of Multiple Myeloma: Results and future perspectives", Seminars in Oncology, Aug. 2002, 29(4), 23-26, Suppl. 13.
Preiss et al., "Pharmacokinetics of bendamustin (Cytostasan) in patients", Pharmazie, Mar. 1985, 40(11), 782-784.
Remington: Pharmaceutical Sciences, 1990, Mack Publishing company, Easton, Pennsylvania.
Ribomustin: Bendamustine Product Monograph, Jan. 2002, 3-58, Ribosepharm GMBH, Munchen, Germany.
Ribomustin: Bendamustine Product Monograph, Mar. 2005, 3-73, Ribosepharm MBH, Munchen, Germany.
Rummel et al., "Bendamustine in the treatment of non-Hodgkin's lymphoma: Results and future perspectives", Seminars in Oncology, Aug. 2002, 29(4), 27-32, Suppl. 13.
Rummel et al., "In Vitro Studies With Bendaustine: Enhanced Activity in Combination With Rituximab", Seminars in Oncology, Aug. 2002, 29(4), 12-14, Suppl. 13.
Scasnar et al., "Radiochemical Assay of Stability of $^{14}$C-Cytostasan Solutions During Preparation and Storage", Journal of Radioanalytical and Nuclear Chemistry, 1998, 121(2), 489-497.
Scasnar et al., "Stability studies of 14C-Cytostasan solutions and its extraction using dicarbolide of cobalt," Die Pharmazie, Mar. 1988, 43(3), 176-179.
Schmidt-Hieber et al., "A phase II study of bendamustine chemotherapy as second-line treatment in metastatic uveal melanoma", Melanoma Research, 2004, 14(6), 439-442.

(56) References Cited

OTHER PUBLICATIONS

Schoffski et al., "Repeated administration of short infusions of Bendamustine: a phase I study in patients with advanced progressive solid tumors", Journal of Cancer Research and Clinical Oncology, 2000, 126(1), 41-47.

Schrijvers et al., "Phase I studies with bendamustine: An update", Seminars in Oncology, 2002, 29(4), 15-18, Suppl. 13.

Schwanen et al., "In Vitro Evaluation of Bendamustine Induced Apoptosis in B-Chronic Lymphocytic Leukemia", Leukemia, Oct. 2002, 16(10), 2096-2105.

Strumberg et al., "Bendamustine hydrochloride activity against doxorubicin-resistant human breast carcinoma eel/lines", Anti-Cancer Drugs, 1996, 7(4), 415-421.

Weide et al., "Bendamustine mitoxantrone and rituximab (BMR): A new effective regimen for refractory or relapsed indolent lymphomas", Leukemia & Lymphoma, 2002, 43(2), 327-331.

Weide et al., "Bendamustine/Mitoxantrone/Rituximab (BMR): A Very Effective, Well Tolerated Outpatient Chemoimmunotherapy for Relapsed and Refractory CD20-positive Indolent Malignancies. Final Results of a Pilot Study", Leukemia & Lymphoma, 2004, 45(12), 2445-2449.

Weidmann et al., "Bendamustine is Effective in Relapsed or Refractory Aggressive non-Hodgkin's Lymphoma", Annals of Oncology, Aug. 2002, 13(8), 1285-1289.

Werner et al., "Hydrolyseprodukte des Cancerostaticums Cytostasan (Bendamustin)", Pharmazie, 1987, 42, 272-273.

Zulkowski, et al., "Regression of brain metastases from breast carcinoma after chemotherapy with bendamustine", Journal of Cancer Research and Clinical Oncology, 2002, 128(2), 111-113.

Teagarden et al., "Practical aspects of lyophilization using non-aqueous co-solvent systems," European Journal of Pharmaceutical Sciences, Mar. 2002, 15(2), 115-133.

Wittaya-Areekul et al., "Freeze-drying of tert-butyl alcohol/water cosolvent systems: Effects of formulation and process variables on residual solvents," Journal of Pharmaceutical Sciences, Apr. 1998, 87(4), 491-495.

U.S. Appl. No. 13/719,409, filed Dec. 19, 2012, Cephalon, Inc.

* cited by examiner

BENDAMUSTINE PHARMACEUTICAL COMPOSITIONS

CROSS REFERENCE TO RELATED APPLICATIONS

This application is a continuation of U.S. application Ser. No. 13/654,898, filed Oct. 18, 2012, which is a continuation of U.S. application Ser. No. 11/330,868, filed Jan. 12, 2006, which claims the benefit of U.S. Provisional Application No. 60/644,354, filed Jan. 14, 2005, the entireties of which are incorporated herein for all purposes.

FIELD OF THE INVENTION

The present invention pertains to the field of pharmaceutical compositions for the treatment of various disease states, especially neoplastic diseases and autoimmune diseases. Particularly, it relates to pharmaceutical formulations comprising nitrogen mustards, particularly the nitrogen mustard bendamustine, e.g., bendamustine HCl.

BACKGROUND OF THE INVENTION

The present invention claims the benefit of and priority to U.S. Ser. No. 60/644,354, filed Jan. 14, 2005, entitled, "Bendamustine Pharmaceutical Compositions," which is incorporated herein by reference in its entirety, including figures and claims.

The following description includes information that may be useful in understanding the present invention. It is not an admission that any such information is prior art, or relevant, to the presently claimed inventions, or that any publication specifically or implicitly referenced is prior art.

Because of their high reactivity in aqueous solutions, nitrogen mustards are difficult to formulate as pharmaceuticals and are often supplied for administration in a lyophilized form that requires reconstitution, usually in water, by skilled hospital personal prior to administration. Once in aqueous solution, nitrogen mustards are subject to degradation by hydrolysis, thus, the reconstituted product should be administered to a patient as soon as possible after its reconstitution.

Bendamustine, (4-{5-[Bis(2-chloroethyl)amino]-1-methyl-2-benzimidazolyl}butyric acid, is an atypical structure with a benzimidazole ring, whose structure includes an active nitrogen mustard (see Formula I, which shows bendamustine hydrochloride).

Formula I

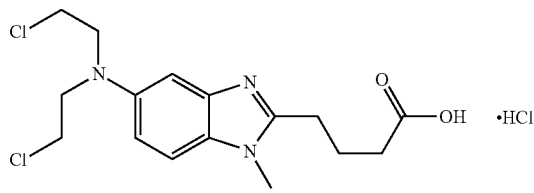

Bendamustine was initially synthesized in 1963 in the German Democratic Republic (GDR) and was available from 1971 to 1992 in that location under the name Cytostasan®. Since that time, it has been marketed in Germany under the tradename Ribomustin®. It has been widely used in Germany to treat chronic lymphocytic leukemia, Hodgkin's disease, non-Hodgkin's lymphoma, multiple myeloma, and breast cancer.

Due to its degradation in aqueous solutions (like other nitrogen mustards), bendamustine is supplied as a lyophilized product. The current lyophilized formulation of bendamustine (Ribomustin®) contains bendamustine hydrochloride and mannitol in a sterile lyophilized form as a white powder for intravenous use following reconstitution. The finished lyophilisate is unstable when exposed to light. Therefore, the product is stored in brown or amber-colored glass bottles. The current lyophilized formulation of bendamustine contains degradation products that may occur during manufacturing of the drug substance and/or during the lyophilization process to make the finished drug product.

Currently bendamustine is formulated as a lyophilized powder for injection with 100 mg of drug per 50 mL vial or 25 mg of drug per 20 mL vial. The vials are opened and reconstituted as close to the time of patient administration as possible. The product is reconstituted with 40 mL (for the 100 mg presentation) or 10 mL (for the 25 mg presentation) of Sterile Water for Injection. The reconstituted product is further diluted into 500 mL, q.s., 0.9% Sodium Chloride for Injection. The route of administration is by intravenous infusion over 30 to 60 minutes.

Following reconstitution with 40 mL Sterile Water for Injection, vials of bendamustine are stable for a period of 7 hours under room temperature storage or for 6 days upon storage at 2-8° C. The 500 mL admixture solution must be administered to the patient within 7 hours of vial reconstitution (assuming room temperature storage of the admixture).

The reconstitution of the present bendamustine lyophilized powder is difficult. Reports from the clinic indicate that reconstitution can require at least fifteen minutes and may require as long as thirty minutes. Besides being burdensome and time-consuming for the healthcare professional responsible for reconstituting the product, the lengthy exposure of bendamustine to water during the reconstitution process increases the potential for loss of potency and impurity formation due to the hydrolysis of the product by water.

Thus, a need exists for lyophilized formulations of bendamustine that are easier to reconstitute and which have a better impurity profile than the current lyophilate (lyophilized powder) formulations of bendamustine.

German (GDR) Patent No. 34727 discloses a method of preparing ω-[5-bis-(β-chloroethyl)-amino-benzimidazolyl-(2)]-alkane carboxylic acids substituted in the 1-position.

German (GDR) Patent No. 80967 discloses an injectable preparation of γ-[1-methyl-5-bis-(β-chloroethyl)-amino-benzimaidazolyl-(2)]-butric acid hydrochloride.

German (GDR) Patent No. 159877 discloses a method for preparing 4-[1-methyl-5-bis(2-chloroethyl)amino-benzimidazolyl-2)-butyric acid.

German (GDR) Patent No. 159289 discloses an injectable solution of bendamustine.

Ribomustin® bendamustine Product monograph (updated January 2002) http://www.ribosepharm.de/pdf/ribomustin_bendamustin/productmonograph.pdf provides information about Ribomustin® including product description.

Ni et al. report that the nitrosourea SarCNU was more stable in pure tertiary butanol than in pure acetic acid, dimethyl sulfoxide, methylhydroxy, water or in TBA/water mixtures (Ni et al. (2001) *Intl. J. Phamaceutics* 226:39-46).

Lyophilized cyclophoshamide is known in the art see e.g., U.S. Pat. Nos. 5,418,223; 5,413,995; 5,268,368; 5,227,374; 5,130,305; 4,659,699; 4,537,883; and 5,066,647.

The lyophilized nitrogen mustard Ifosfamide is disclosed in International Publication No. WO 2003/066027; U.S. Pat. Nos. 6,613,927; 5,750,131; 5,972,912; 5,227,373; and 5,204,335.

Teagarden et al. disclose lyophilized formulations of prostaglandin E-1 made by dissolving PGE-1 in a solution of lactose and tertiary butyl alcohol (U.S. Pat. No. 5,770,230).

SUMMARY OF THE INVENTION

The present invention is directed to stable pharmaceutical compositions of nitrogen mustards, in particular lyophilized bendamustine and its use in treatment of various disease states, especially neoplastic diseases and autoimmune diseases.

An embodiment of the invention is a pharmaceutical composition of bendamustine containing not more than about 0.5% to about 0.9% (area percent of bendamustine) HP1, as shown in Formula II, Formula II

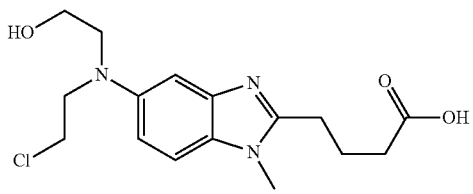

at the time of release or where the HP1 is the amount of HP1 present at time zero after reconstitution of a lyophilized pharmaceutical composition of bendamustine as described herein. In a preferred embodiment is a pharmaceutical composition of bendamustine containing not more than about 0.5% (area percent of bendamustine) HP1, preferably not more than about 0.45%, more preferably not more than about 0.40%, more preferably not more than about 0.35%, even more preferably not more than 0.30%.

Another embodiment of the invention is a lyophilized preparation of bendamustine containing not more than about 0.1% to about 0.3% bendamustine dimer as shown in Formula III at release or at time zero after reconstitution Formula III

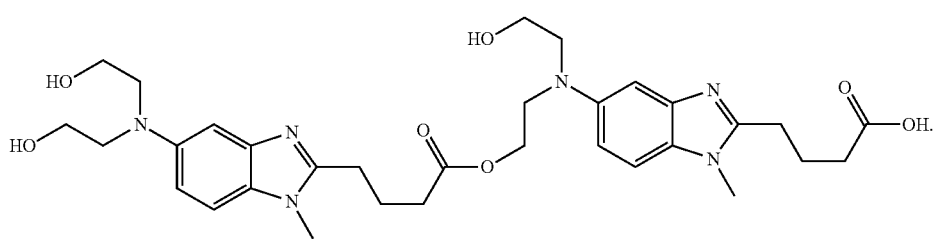

Yet another embodiment of the invention is a lyophilized preparation of bendamustine containing not more than about 0.5%, preferably 0.15% to about 0.5%, bendamustine ethylester, as shown in Formula IV at release or at time zero after reconstitution Formula IV

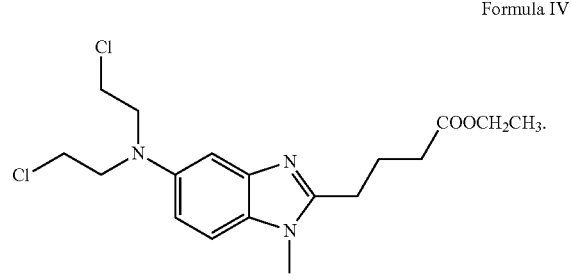

Yet another embodiment of the invention is a lyophilized preparation of bendamustine wherein the concentration of bendamustine ethylester (Formula IV) is no more than 0.2%, preferably 0.1%, greater than the concentration of bendamustine ethylester as found in the drug substance used to make the lyophilized preparation.

In another embodiment of the invention is a lyophilized preparation of bendamustine containing not more than about 0.5% to about 0.9% (area percent of bendamustine) HP1 at the time of drug product release. In a preferred embodiment is a lyophilized preparation of bendamustine containing not more than about 0.50% (area percent of bendamustine) HP1, preferably not more than about 0.45%, more preferably not more than about 0.40%, more preferably not more than about 0.35%, even more preferably not more than about 0.30%. An aspect of this embodiment is lyophilized preparations of bendamustine containing not more than about 0.5% to about 0.9%, preferably 0.5%, (area percent of bendamustine) HP1 at the time of release of drug product where the lyophilized preparation is packaged in a vial or other pharmaceutically acceptable container.

In yet another aspect of the invention, the lyophilized preparations of bendamustine are stable with respect to the amount of HP1 for at least about 6 months, preferably 12 months, preferably 24 months, to about 36 months or greater when stored at about 2° to about 30°. Preferred temperatures for storage are about 5° C. and about room temperature.

Another embodiment of the invention is a pharmaceutical dosage form that includes a pharmaceutical composition of bendamustine containing not more than about 0.5% to about 0.9% HP1, preferably not more than about 0.50%, preferably not more than about 0.45%, more preferably not more than about 0.40%, more preferably not more than about 0.35%, even more preferably not more than about 0.30%, where the HP1 is the amount of HP1 present at release or at time zero after reconstitution of a lyophilized preparation of bendamustine of the present invention. In preferred aspects of the invention, the dosage form can be about 5 to about 500 mg of bendamustine, about 10 to about 300 mg of bendamustine, about 25 mg of bendamustine, about 100 mg of bendamustine, and about 200 mg of bendamustine.

Yet another embodiment of the invention is a pharmaceutical dosage form that includes a lyophilized preparation of bendamustine containing not more than about 0.5% to about 0.9%, preferably 0.5%, HP1. Preferred dosage forms can be about 5 to about 500 mg of bendamustine, about 10 to about 300 mg of bendamustine, about 25 mg of bendamustine, about 100 mg of bendamustine, and about 200 mg of bendamustine.

In still another embodiment, the invention includes a pharmaceutical composition of bendamustine including bendamustine containing not more than about 0.5% to about 0.9% (area percent of bendamustine), preferably not more than about 0.50%, preferably not more than about 0.45%, more preferably not more than about 0.40%, more preferably not more than about 0.35%, even more preferably not more than 0.30%, and a trace amount of one or more organic solvents, wherein said HP1 is the amount of HP1 present at release or time zero after reconstitution of a lyophilized pharmaceutical composition of bendamustine as disclosed herein. In different aspects of this embodiment, the organic solvent is selected from one or more of tertiary butanol, n-propanol, n-butanol, isopropanol, ethanol, methanol, acetone, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, hexafluoroacetone, chlorobutanol, dimethyl sulfone, acetic acid, and cyclohexane. Preferred organic solvents include one or more of ethanol, methanol, propanol, butanol, isopropanol, and tertiary butanol. A more preferred organic solvent is tertiary butanol, also known as TBA, t-butanol, tert-butyl alcohol or tertiary butyl alcohol.

The present invention involves a method for obtaining agency approval for a bendamustine product, the improvement which includes setting a release specification for bendamustine degradants at less than about 4.0%, preferably about 2.0% to about 4.0%, (area percent bendamustine) or otherwise to achieve the pharmaceutical compositions described herein. An aspect of this embodiment is a method for obtaining agency approval for a bendamustine product which includes setting a release specification for HP1 to be less than or equal to 1.5% (area percent Bendamustine). The bendamustine product herein contains not more than about 0.5% (area percent of bendamustine) HP1 at release.

Another embodiment is a method for obtaining agency approval for a bendamustine product, the improvement which includes setting a shelf-life specification for bendamustine degradants at less than about 7.0%, preferably about 5.0% to about 7.0%, (area percent bendamustine) where the product is stored at about 2° C. to about 30° C. Preferred temperatures for storage are about 5° C. and about room temperature. The bendamustine product herein contains not more than about 0.5% (area percent of bendamustine) HP1 at release.

Another embodiment of the invention is a process for manufacturing a lyophilized preparation of bendamustine which includes controlling for the concentration of bendamustine degradants in the final product, such that the concentration of bendamustine degradants is less than about 4.0%, preferably no more than about 2.0% to about 4.0%, (area percent of bendamustine) at release or otherwise to achieve the pharmaceutical compositions described herein. The bendamustine product herein contains not more than about 0.5% to about 0.9%, preferably about 0.5%, (area percent of bendamustine) HP1 at release.

The present invention discloses a process for manufacturing a lyophilized preparation of bendamustine which comprises controlling for the concentration of bendamustine degradants in the final product, such that, at release, the concentration of HP1 is less than 0.9%, preferably 0.5%, (area percent of bendamustine) and, at the time of product expiration, the concentration of bendamustine degradants is less than about 7.0%, preferably no more than about 5.0% to about 7.0%; wherein said product is stored at about 2° C. to about 30° C.

Another embodiment of the invention is a bendamustine pre-lyophilization solution or dispersion comprising one or more organic solvents where the solution or dispersions include at least one stabilizing concentration of an organic solvent which reduces the level of degradation of bendamustine so that the amount of HP1 produced during lyophilization from about 0 to 24 hours does not exceed about 0.5% to about 0.9% (area percent of bendamustine) preferably 0.50%, preferably 0.45%, more preferably 0.40%, more preferably 0.35%, even more preferably 0.30%. An aspect of this embodiment is the lyophilized powder produced from the pre-lyophilization solution or dispersion.

Still another embodiment of the invention is a bendamustine pre-lyophilization solution or dispersion comprising one or more organic solvents where the solution or dispersions include at least one stabilizing concentration of an organic solvent which reduces the level of degradation of bendamustine so that the amount of bendamustine ethylester produced during lyophilization from about 0 to 24 hours does not exceed about 0.5% (area percent bendamustine). An aspect of this embodiment is the lyophilized powder produced from the pre-lyophilization solution or dispersion.

Still another embodiment of the invention is a bendamustine pre-lyophilization solution or dispersion comprising one or more organic solvents where the solution or dispersions include at least one stabilizing concentration of an organic solvent which reduces the level of degradation of bendamustine so that the amount of bendamustine ethylester (as shown in Formula IV) produced during lyophilization from about 0 to 24 hours is no more than 0.2%, preferably 0.1%, greater than the concentration of bendamustine ethylester as found in the drug substance used to make the pre-lyophilization solution. A preferred organic solvent is tertiary butanol.

The invention also discloses methods for preparing a bendamustine lyophilized preparation that includes dissolving bendamustine in a stabilizing concentration of an alcohol solvent of between about 5% to about 100% (v/v alcohol to form a pre-lyophilization solution; and lyophilizing the pre-lyophilization solution; wherein the bendamustine lyophilized preparation made from such methods contains not more than about 0.5% to about 0.9%, preferably 0.5%, (area percent of bendamustine) HP1 as shown in Formula II, wherein said HP1 is the amount of HP1 present at release or at time zero after reconstitution of the lyophilized pharmaceutical composition of bendamustine. Other alcohol concentrations include about 5% to about 99.9%, about 5% to about 70%, about 5% to about 60%, about 5% to about 50%, about 5% to about 40%, about 20% to about 35%. Preferred concentrations of alcohol are from about 20% to about 30%. Preferred alcohols include one or more of methanol, ethanol, propanol, iso-propanol, butanol, and tertiary-butanol. A more preferred alcohol is tertiary-butanol. A preferred concentration of tertiary-butanol is about 20% to about 30%, preferably about 30%. An aspect of this embodiment is the addition of an excipient before lyophilization. A preferred excipient is mannitol. Preferred pre-lyophilized concentrations of bendamustine are from about 2 mg/mL to about 50 mg/mL.

In a preferred method for preparing a bendamustine lyophilized preparation, lyophilizing the pre-lyophilization solution comprises i) freezing the pre-lyophilization solution to a temperature below about −40° C., preferably −50° C., to form a frozen solution; ii) holding the frozen solution at or below −40° C., preferably −50° C., for at least 2 hours; iii) ramping the frozen solution to a primary drying temperature between about −40° C. and about −10° C. to form a dried solution; iv) holding for about 10 to about 70 hours; v) ramping the dried solution to a secondary drying temperature between about 25° C. and about 40° C.; and vii) holding for about 5 to about 40 hours to form a bendamustine lyophilized preparation. In a more preferred method lyophilizing the pre-lyophilization solution comprises i) freezing the pre-lyophilization solution to about −50° C. to form a frozen solution; ii) holding the frozen solution at about −50° C. for at least 2 hours to about 4 hours; iii) ramping to a primary drying temperature between about −20° C. and about −12° C. to form a dried solution; iv)

holding at a primary drying temperature for about 10 to about 48 hours; v) ramping the dried solution to a secondary drying temperature between about 25° C. and about 40° C.; and vi) holding at a secondary drying temperature for at least 5 hours up to about 20 hours. A preferred alcohol is tertiary-butanol. A preferred concentration of tertiary-butanol is about 20% to about 30%, preferably about 30%. An aspect of this embodiment is the addition of an excipient before lyophilization. A preferred excipient is mannitol. Preferred pre-lyophilized concentrations of bendamustine are from about 2 mg/mL to about 50 mg/mL.

Another embodiment of the invention is the lyophilized powder or preparation obtained from the methods of preparing a bendamustine lyophilized preparation disclosed herein.

The invention also involves bendamustine formulations for lyophilization that include an excipient and a stabilizing concentration of an organic solvent. A preferred formulation includes bendamustine at a concentration of about 15 mg/mL, mannitol at a concentration of about 25.5 mg/mL, tertiary-butyl alcohol at a concentration of about 30% (v/v) and water. Included in this embodiment of the invention are the lyophilized preparations made from such bendamustine formulations.

Included in the inventions are methods of treating a medical condition in a patient that involve administering a therapeutically effective amount of a pharmaceutical composition of the invention where the condition is amenable to treatment with said pharmaceutical composition. Some conditions amenable to treatment with the compositions of the invention include chronic lymphocytic leukemia (CLL), Hodgkin's disease, non-Hodgkin's lymphoma (NHL), multiple myeloma (MM), breast cancer, small cell lung cancer, hyperproliferative disorders, and an autoimmune disease. Preferred conditions include NHL, CLL, breast cancer, and MM. Preferred autoimmune diseases include rheumatoid arthritis, multiple sclerosis or lupus.

Included in the inventions are the use of the pharmaceutical compositions or pharmaceutical preparations of the invention in the manufacture of a medicament for the treatment of a medical condition, as defined herein, in a patient that involve administering a therapeutically effective amount of a pharmaceutical composition of the invention where the condition is amenable to treatment with said pharmaceutical composition.

Also included in the invention are methods of treating in which the pharmaceutical compositions of the invention are in combination with one or more anti-neoplastic agents where the antineoplastic agent is given prior, concurrently, or subsequent to the administration of the pharmaceutical composition of the invention. Preferred antineoplastic agents are antibodies specific for CD20.

Another embodiment of the invention is a lyophilization cycle for producing lyophilized bendamustine preparations of the invention. A preferred lyophilization cycle includes a) freezing to about −50° C. over about 8 hours; b) holding at −50° C. for about 4 hours; c) ramping to −25° C. over about 3 hours; d) holding at −10° C. for 30 hours; e) ramping to between about 25° C. and about 40° C. or higher for about 3 hours; f) holding between about 25° C. and about 40° C. for about 25 hours; g) ramping to about 20° C. in 1 hour; h) unloading at about 20° C., at a pressure of 13.5 psi in a pharmaceutically acceptable container that is hermetically sealed; wherein the pressure is about 150 microns throughout primary drying and 50 microns throughout secondary drying. An aspect of this cycle involves step (e) which is ramped to about 30-35° C. for 3 hours and then ramped to 40° C. for 5 hours. Another aspect of this embodiment is the lyophilized powered prepared from such lyophilization cycles. A more preferred lyophilization cycle includes i) starting with a shelf temperature of about 5° C. for loading; ii) freezing to about −50° C. over about 8 hours; iii) holding at −50° C. for about 4 hours; iv) ramping to about −20° C. over about 3 hours; v) holding at about −20° C. for 6 hours; ramping to about −15° C. over about 1 hour; vi) holding at −15° C. for about 20 hours; vii) ramping to about −15° C. over about 1 hour; viii) holding at about −15° C. for about 20 hours; ix) ramping to about −12° C. over about 0.5 hours; x) holding at about −12° C. for about 15.5 hours; xi) ramping to between about 25° C. and about 40° C. or higher for about 15 hours; xii) holding between about 25° C. and about 40° C. for about 10 hours; xiii) ramping to about 40° C. over about 1 hour; and xiv) holding at about 40° C. for about 5 hours; unloading at about 5° C., at a pressure of about 13.5 psi in a pharmaceutically acceptable container that is hermetically sealed; wherein the pressure is about 150 microns throughout primary drying and 50 microns throughout secondary drying. In a preferred embodiment step (xi) is ramped to about 30-35° C. for about 15 hours.

The invention also encompasses a pharmaceutical dosage form of bendamustine containing not more than about 0.5% to about 0.9%, preferably 0.5%, HP1 (area percent of bendamustine) wherein said dosage form comprises a vial or other pharmaceutically acceptable container, wherein said HP1 is the amount of HP1 present pre-reconstitution or at time zero after reconstitution of said dosage form. Preferred concentrations of bendamustine include about 10 to about 500 mg/container, about 100 mg/container, about 5 mg to about 2 g/container and about 170 mg/container.

The present invention also includes pre-lyophilized pharmaceutical compositions of bendamustine. A preferred pre-lyophilized composition includes bendamustine HCl about 15 mg/mL, mannitol about 25.5 mg/mL, about 30% (v/v) tertiary-butyl alcohol, and water.

These and other embodiments of the invention are described hereinbelow or are evident to persons of ordinary skill in the art based on the following disclosures.

DETAILED DESCRIPTION OF THE INVENTION

Figure 1:
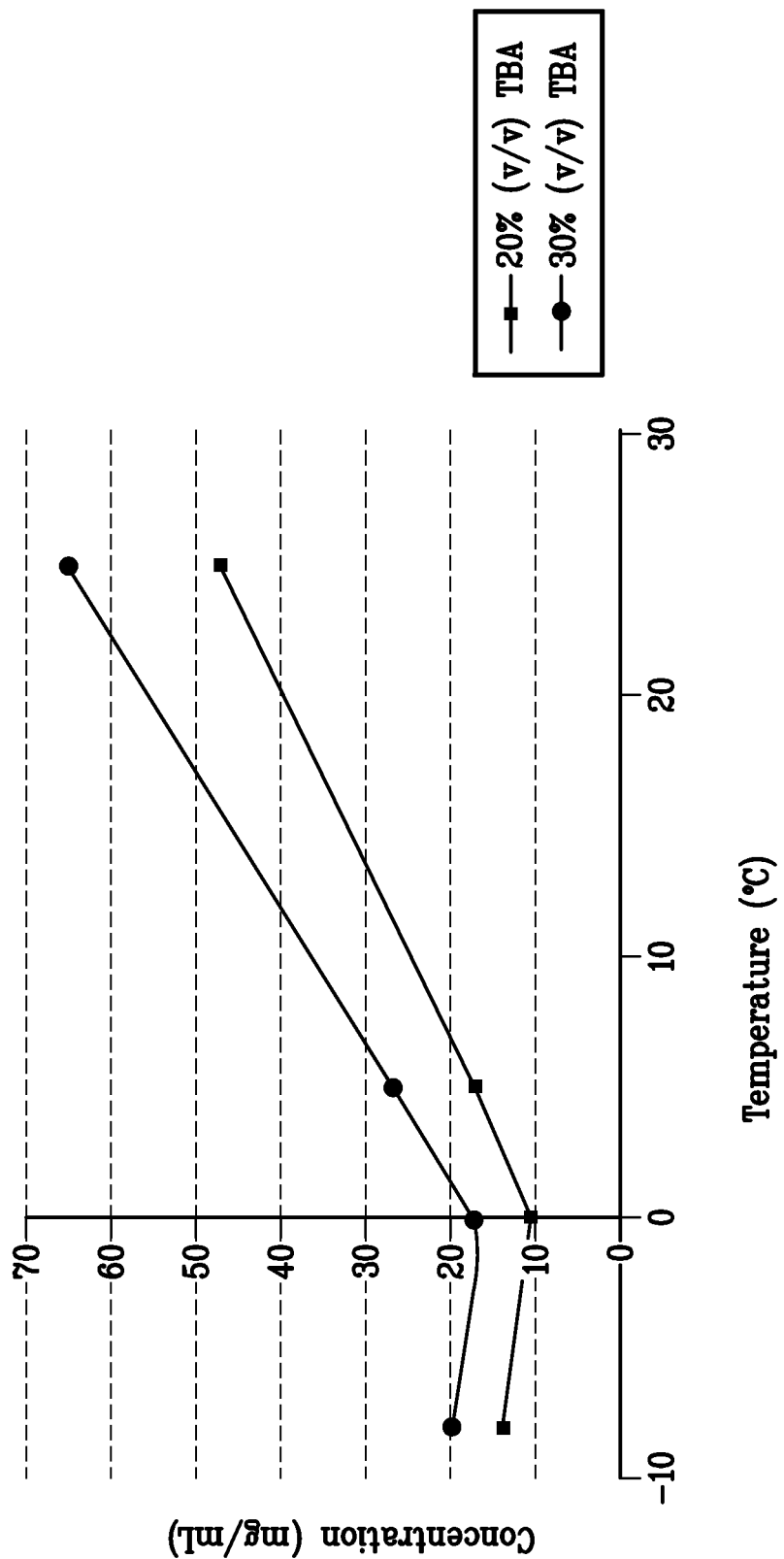
FIG. 1 shows the solubility of bendamustine at various temperatures for two different solutions of bendamustine in tertiary butanol.

As used herein, the terms "formulate" refers to the preparation of a drug, e.g., bendamustine, in a form suitable for administration to a mammalian patient, preferably a human. Thus, "formulation" can include the addition of pharmaceutically acceptable excipients, diluents, or carriers.

As used herein, the term "lyophilized powder" or "lyophilized preparation" refers to any solid material obtained by lyophilization, i.e., freeze-drying of an aqueous solution. The aqueous solution may contain a non-aqueous solvent, i.e. a solution composed of aqueous and one or more non-aqueous solvent(s). Preferably, a lyophilized preparation is one in which the solid material is obtained by freeze-drying a solution composed of aqueous and one or more non-aqueous solvents, more preferably the non-aqueous solvent is an alcohol.

By "stable pharmaceutical composition" is meant any pharmaceutical composition having sufficient stability to have utility as a pharmaceutical product. Preferably, a stable pharmaceutical composition has sufficient stability to allow storage at a convenient temperature, preferably between $-20°$ C. and $40°$ C., more preferably about $2°$ C. to about $30°$ C., for a reasonable period of time, e.g., the shelf-life of the product which can be as short as one month but is typically six months or longer, more preferably one year or longer even more preferably twenty-four months or longer, and even more preferably thirty-six months or longer. The shelf-life or expiration can be that amount of time where the active ingredient degrades to a point below 90% purity. For purposes of the present invention stable pharmaceutical composition includes reference to pharmaceutical compositions with specific ranges of impurities as described herein. Preferably, a stable pharmaceutical composition is one which has minimal degradation of the active ingredient, e.g., it retains at least about 85% of un-degraded active, preferably at least about 90%, and more preferably at least about 95%, after storage at $2-30°$ C. for a 2-3 year period of time.

By "stable lyophilized preparation" is meant any lyophilized preparation having sufficient stability, such characteristics as similarly defined herein for a stable pharmaceutical composition, to have utility as a pharmaceutical product By "degraded" is meant that the active has undergone a change in chemical structure.

The term "therapeutically effective amount" as used herein refers to that amount of the compound being administered that will relieve to some extent one or more of the symptoms of the disorder being treated. In reference to the treatment of neoplasms, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or (4) relieving to some extent (or, preferably, eliminating) one or more symptoms associated with the cancer. Therapeutically effective amount can also mean preventing the disease from occurring in an animal that may be predisposed to the disease but does not yet experience or exhibit symptoms of the disease (prophylactic treatment). Further, therapeutically effective amount can be that amount that increases the life expectancy of a patient afflicted with a terminal disorder. Typical therapeutically effective doses for bendamustine for the treatment of non-Hodgkin's lymphoma can be from about $60\text{-}120\text{ mg/m}^2$ given as a single dose on two consecutive days. The cycle can be repeated about every three to four weeks. For the treatment of chronic lymphocytic leukemia (CLL) bendamustine can be given at about $80\text{-}100\text{ mg/m}^2$ on days 1 and 2. The cycle can be repeated after about 4 weeks. For the treatment of Hodgkin's disease (stages II-IV), bendamustine can be given in the "DBVBe regimen" with daunorubicin $25\text{ mg/m}^2$ on days 1 and 15, bleomycin $10\text{ mg/m}^2$ on days 1 and 15, vincristine $1.4\text{ mg/m}^2$ on days 1 and 15, and bendamustine $50\text{ mg/m}^2$ on days 1-5 with repetition of the cycle about every 4 weeks. For breast cancer, bendamustine ($120\text{ mg/m}^2$) on days 1 and 8 can be given in combination with methotrexate $40\text{ mg/m}^2$ on days 1 and 8, and 5-fluorouracil $600\text{ mg/m}^2$ on days 1 and 8 with repetition of the cycle about every 4 weeks. As a second-line of therapy for breast cancer, bendamustine can be given at about $100\text{-}150\text{ mg/m}^2$ on days 1 and 2 with repetition of the cycle about every 4 weeks.

As used herein "neoplastic" refers to a neoplasm, which is an abnormal growth, such growth occurring because of a proliferation of cells not subject to the usual limitations of growth. As used herein, "anti-neoplastic agent" is any compound, composition, admixture, co-mixture, or blend which inhibits, eliminates, retards, or reverses the neoplastic phenotype of a cell.

As used herein "hyperproliferation" is the overproduction of cells in response to a particular growth factor. "Hyperproliferative disorders" are diseases in which the cells overproduce in response to a particular growth factor. Examples of such "hyperproliferative disorders" include diabetic retinopathy, psoriasis, endometriosis, cancer, macular degenerative disorders and benign growth disorders such as prostate enlargement.

As used herein, the term "vial" refers to any walled container, whether rigid or flexible.

"Controlling" as used herein means putting process controls in place to facilitate achievement of the thing being controlled. For example, in a given case, "controlling" can mean testing samples of each lot or a number of lots regularly or randomly; setting the concentration of degradants as a release specification; selecting process conditions, e.g., use of alcohols and/or other organic solvents in the pre-lyophilization solution or dispersion, so as to assure that the concentration of degradants of the active ingredient is not unacceptably high; etc. Controlling for degradants by setting release specifications for the amount of degradants can be used to facilitate regulatory approval of a pharmaceutical product by a regulatory agency, such as the U.S. Food and Drug Administration and similar agencies in other countries or regions ("agency").

The term "pharmaceutically acceptable" as used herein means that the thing that is pharmaceutically acceptable, e.g., components, including containers, of a pharmaceutical composition, does not cause unacceptable loss of pharmacological activity or unacceptable adverse side effects. Examples of pharmaceutically acceptable components are provided in The United States Pharmacopeia (USP), The National Formulary (NF), adopted at the United States Pharmacopeial Convention, held in Rockville, Md. in 1990 and FDA Inactive Ingredient Guide 1990, 1996 issued by the U.S. Food and Drug Administration (both are hereby incorporated by reference herein, including any drawings). Other grades of solutions or components that meet necessary limits and/or specifications that are outside of the USP/NF may also be used.

The term "pharmaceutical composition" as used herein shall mean a composition that is made under conditions such that it is suitable for administration to humans, e.g., it is made under GMP conditions and contains pharmaceutically acceptable excipients, e.g., without limitation, stabilizers, bulking agents, buffers, carriers, diluents, vehicles, solubilizers, and binders. As used herein pharmaceutical composition includes but is not limited to a pre-lyophilization solution or dispersion as well as a liquid form ready for injection or infusion after reconstitution of a lyophilized preparation.

A "pharmaceutical dosage form" as used herein means the pharmaceutical compositions disclosed herein being in a container and in an amount suitable for reconstitution and administration of one or more doses, typically about 1-2, 1-3, 1-4, 1-5, 1-6, 1-10, or about 1-20 doses. Preferably, a "pharmaceutical dosage form" as used herein means a lyophilized pharmaceutical composition disclosed herein in a container and in an amount suitable for reconstitution and delivery of one or more doses, typically about 1-2, 1-3, 1-4, 1-5, 1-6, 1-10, or about 1-20 doses. The pharmaceutical dosage form can comprise a vial or syringe or other suitable pharmaceutically acceptable container. The pharmaceutical dosage form suitable for injection or infusion use can include sterile aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The prevention of the growth of microorganisms can be accomplished by various antibacterial and antifungal agents, for example, parabens, chlorobutanol, phenol, sorbic acid, thimerosal, and the like.

As used herein, the term "excipient" means the substances used to formulate active pharmaceutical ingredients (API) into pharmaceutical formulations; in a preferred embodiment, an excipient does not lower or interfere with the primary therapeutic effect of the API. Preferably, an excipient is therapeutically inert. The term "excipient" encompasses carriers, diluents, vehicles, solubilizers, stabilizers, bulking agents, and binders. Excipients can also be those substances present in a pharmaceutical formulation as an indirect or unintended result of the manufacturing process. Preferably, excipients are approved for or considered to be safe for human and animal administration, i.e., GRAS substances (generally regarded as safe). GRAS substances are listed by the Food and Drug administration in the Code of Federal Regulations (CFR) at 21 CFR §182 and 21 CFR §184, incorporated herein by reference. Preferred excipients include, but are not limited to, hexitols, including mannitol and the like.

As used herein "a stabilizing concentration of an organic solvent" or "a stabilizing concentration of an alcohol" means that amount of an organic solvent or alcohol that reduces the level of degradation of bendamustine to achieve a specified level of degradants in the final drug product. For example, with respect to the degradant HP1, a stabilizing concentration of an organic solvent is that amount which results in an HP1 concentration (area percent of bendamustine) of less than about 0.5%, preferably less than 0.45%, preferably less than 0.40%, more preferably less than 0.35%, more preferably less than 0.30%, and even more preferably less than 0.25%. With respect to the overall or total degradant concentration of the final drug product, a stabilizing concentration of an organic solvent is that amount that results in a total degradant concentration (at the time of drug product release) of less than about 7% (area percent bendamustine), preferably less than about 6%, more preferably less than about 5%, and even more preferably less than about 4.0%. By "area percent of bendamustine" is meant the amount of a specified degradant, e.g., HP1, relative to the amount of bendamustine as determined, e.g., by HPLC.

The term "organic solvent" means an organic material, usually a liquid, capable of dissolving other substances.

As used herein, "trace amount of an organic solvent" means an amount of solvent that is equal to or below recommended levels for pharmaceutical products, for example, as recommended by ICH guidelines (International Conferences on Harmonization, Impurities—Guidelines for Residual Solvents. Q3C. Federal Register. 1997; 62(247):67377). The lower limit is the lowest amount that can be detected.

The term "release" or "at release" means the drug product has met the release specifications and can be used for its intended pharmaceutical purpose.

A. General

The invention provides stable, pharmaceutically acceptable compositions prepared from bendamustine. In particular, the invention provides formulations for the lyophilization of bendamustine HCl. The lyophilized powder obtained from such formulations is more easily reconstituted than the presently available lyophilized powder of bendamustine. Further, the lyophilized products of the present invention have a better impurity profile than Ribomustin® with respect to certain impurities, in particular HP1, bendamustine dimer, and bendamustine ethylester, prior to reconstitution, upon storage of the lyophilate, or following reconstitution and admixture.

The present invention further provides formulations of bendamustine useful for treating neoplastic diseases. The formulations described herein can be administered alone or in combination with at least one additional anti-neoplastic agent and/or radioactive therapy.

An aspect of the invention is conditions and means for enhancing the stability of bendamustine prior to and during the lyophilization process, upon shelf storage or upon reconstitution.

Anti-neoplastic agents which may be utilized in combination with the formulations of the invention include those provided in the Merck Index 11, pp 16-17, Merck & Co., Inc. (1989) and The Chemotherapy Source Book (1997). Both books are widely recognized and readily available to the skilled artisan.

There are large numbers of antineoplastic agents available in commercial use, in clinical evaluation and in pre-clinical development, which could be selected for treatment of neoplasia by combination drug chemotherapy. Such antineoplastic agents fall into several major categories, namely, antibiotic-type agents, covalent DNA-binding drugs, antimetabolite agents, hormonal agents, including glucocorticoids such as prednisone and dexamethasone, immunological agents, interferon-type agents, differentiating agents such as the retinoids, pro-apoptotic agents, and a category of miscellaneous agents, including compounds such as antisense, small interfering RNA, and the like. Alternatively, other antineoplastic agents, such as metallomatrix proteases (MMP) inhibitors, SOD mimics or alpha$_v$ beta$_3$ inhibitors may be used.

One family of antineoplastic agents which may be used in combination with the compounds of the inventions consists of antimetabolite-type antineoplastic agents. Suitable antimetabolite antineoplastic agents may be selected from the group consisting of alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with the compounds of the invention consists of covalent DNA-binding agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol.

Another family of antineoplastic agents which may be used in combination with the compounds disclosed herein consists of antibiotic-type antineoplastic agents. Suitable antibiotic-type antineoplastic agents may be selected from the group consisting of Taiho 4181-A, aclarubicin, actinomycin D, actinoplanone, alanosine, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with the compounds of the invention include a miscellaneous family of antineoplastic agents selected from the group consisting of alpha-carotene, alpha-difluoromethyl-arginine, acitretin, arsenic trioxide, Avastin® (bevacizumab), Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, epothionesTsumura EPMTC, erbitux, ergotamine, erlotnib, etoposide, etretinate, fenretinide, Fujisawa FR-57704, gallium nitrate, genkwadaphnin, Gleevec® (imatnib), Chugai GLA-43, Glaxo GR-63178, gefitinib, grifolan NMF-5N, hexadecylphosphocholine, Green Cross HO-221, homoharringtonine, hydroxyurea, BTG ICRF-187, indanocine, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, mefloquine, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, Rituxan® (and other anti CD20 antibodies, e.g. Bexxar®, Zevalin®), SmithKline SK&F-104864, statins (Lipitor® etc.), Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Thalidomide, Thalidomide analogs, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534, Zometa®.

Examples of radioprotective agents which may be used in the combination chemotherapy of this invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron and Enzon).

Methods for preparation of the antineoplastic agents described above may be found in the literature. Methods for preparation of doxorubicin, for example, are described in U.S. Pat. Nos. 3,590,028 and 4,012,448. Methods for preparing metallomatrix protease inhibitors are described in EP 780386. Methods for preparing .alpha.$_v$ .beta.$_3$ inhibitors are described in WO 97/08174.

Preferred anti-neoplastic agents include, without limitation, one or more of daunorubicin, bleomycin, vincristine, doxorubicin, dacarbazine, prednisolone, mitoxantrone, prednisone, methotrexate, 5-fluorouracil, dexamethasone, thalidomide, thalidomide derivatives, 2ME2, Neovastat, R 11 5777, arsenic trioxide, bortezomib, tamoxifen, G3139 (antisense), and SU5416, mitomycin, anti-CD20 antibodies, such as Rituxan® and R-etodolac.

Preferred drug regimens for which the present formulation may be used in conjunction with or as a replacement for one or more of the components includes, without limitation, ABVD (doxorubicin, bleomycin, vincristine, dacarbazine), DBV (daunorubicin, belomycin, vincristine), CVPP (cyclophosphamide, vinblastine, procarbazine, prednisolone), COP (cyclophosphamide, vincristine, prednisolone), CHOP (cyclophosphamide, doxorubicin, vincristine and prednisone) and CMF (cyclophosphamide, methotrexate, 5-fluorouracil). Additional regimens are given in Table A below.

TABLE A

Cancer Therapeutic Regimens

| Abbreviation | Drugs Used | Disease |
| --- | --- | --- |
| AC | Doxorubicin & Cyclophosphamide | Breast cancer |
| CFM (CF, FNC) | Cyclophosphamide, Fluorouracil, Mitaxantrone | Breast cancer |
| CMF | Cyclophosphamide, Methotrexate, Fluorouracil | Breast cancer |
| NFL | Mitoxantrone, Fluorouracil, Leucovorin | Breast cancer |
| Sequential Dox-CMF | Doxorubicin | Breast cancer |
| VATH | Vinblastine, Doxorubicin, Thiotepa, Fluoxymesterone | Breast cancer |
| EMA-86 | Etoposide, Mitoxantrone, Ctyarabine | AML (induction) |
| 7 + 3 | Cytarabine WITH Daunorubicin OR Idarobicin OR Mitoxantrone | AML (induction) |
| 5 + 2 | Cytarabine WITH Daunorubicin OR Mitoxantrone | AML (induction) |
| HiDAC | Cytarabine | AML (post-remission) |
| ABVD | Doxorubicin, Bleomycin, Vinblastine, Dacarbazine | Hodgkin's |
| ChlVPP | Chlorambucil, Vinblastine, Procarbazine, Prednisone | Hodgkin's |
| EVA | Etoposide, Vinblastine, Doxorubicin | Hodgkin's |
| MOPP | Mechlorethamine, Vincristine, Procarbazine, Prednisone | Hodgkin's |
| MOPP/ABV Hybrid | Mechlorethamine, Vincristine, Procarbazine, Prednisone, Doxorubicin, Bleomycin, Vinblastine | Hodgkin's |
| MOPP/ABVD | Mechlorethamine, Doxorubicin, Vinblastine, Bleomycin, Etoposide, Prednisone | Hodgkin's |
| CNOP | Cyclophosphamide, Mitoxantrone, Vincristine, Prednisone | Non-Hodgkin's |
| COMLA | Cyclophosphamide, Vincristine, Methotrexate, Leucovorin, Cytarabine | Non-Hodgkin's |
| DHAP | Dexamethasone, Cisplatin, Cytarabine | Non-Hodgkin's |

TABLE A-continued

Cancer Therapeutic Regimens

| Abbreviation | Drugs Used | Disease |
| --- | --- | --- |
| ESHAP | Etoposide, Methylprednisilone, Cisplatin, Cytarabine | Non-Hodgkin's |
| MACOP-B | Methotrexate, Leucovorin, Doxorubicin, Cyclophosphamide, Vincristine, Prednisone, Bleomycin, Septra, Ketoconazole | Non-Hodgkin's |
| m-BACOD | Methotrexate, Leucovorin, Bleomycin, Doxorubicin, Cyclophosphamide, Vincristine, Dexamethasone | Non-Hodgkin's |
| MINE-ESHAP | Mesna, Ifosfamide, Mitoxantrone, Etoposide | Non-Hodgkin's |
| NOVP | Mitoxantrone, Vinblastine, Prednisone, Vincristine | Non-Hodgkin's |
| ProMACE/ cytaBOM | Prednisone, Doxorubicin, Cyclophosphamide, Etoposide, Cytarabine, Bleomycin, Vincristine, Methotrexate, Leucovorin, Septra | Non-Hodgkin's |
| M2 | Vincristine, Carmustine, Cyclophosphamide, Melphalan, Prednisone | Multiple Myeloma |
| MP | Melphalan, Prednisone | Multiple Myeloma |
| VAD | Vincristine, Doxorubicin, Dexamethasone | Multiple Myeloma |
| VBMCP | Vincristine, Carmustine, Melphalan, Cyclophosphamide, Prednisone | Multiple Myeloma |

As described herein, a lyophilized formulation of bendamustine is achieved following removal of an organic solvent in water. The most typical example of the solvent used to prepare this formulation is tertiary butanol (TBA). Other organic solvents can be used including ethanol, n-propanol, n-butanol, isoproponal, ethyl acetate, dimethyl carbonate, acetonitrile, dichloromethane, methyl ethyl ketone, methyl isobutyl ketone, acetone, 1-pentanol, methyl acetate, methanol, carbon tetrachloride, dimethyl sulfoxide, hexafluoroacetone, chlorobutanol, dimethyl sulfone, acetic acid, cyclohexane. These preceding solvents may be used individually or in combination. Useful solvents must form stable solutions with bendamustine and must not appreciably degrade or deactivate the API. The solubility of bendamustine in the selected solvent must be high enough to form commercially useful concentrations of the drug in solvent. Additionally, the solvent should be capable of being removed easily from an aqueous dispersion or solution of the drug product, e.g., through lyophilization or vacuum drying. Preferably, a solution having a concentration of about 2-80 mg/mL, preferably about 5 to 40 mg/mL, more preferably 5-20 mg/mL and even more preferably 12 to 17 mg/mL bendamustine is used.

A pharmaceutically acceptable lyophilization excipient can be dissolved in the aqueous phase. Examples of excipients useful for the present invention include, without limitation, sodium or potassium phosphate, citric acid, tartaric acid, gelatin, glycine, and carbohydrates such as lactose, sucrose, maltose, glycerin, dextrose, dextran, trehalose and hetastarch. Mannitol is a preferred excipient. Other excipients that may be used if desired include antioxidants, such as, without limitation, ascorbic acid, acetylcysteine, cysteine, sodium hydrogen sulfite, butyl-hydroxyanisole, butyl-hydroxytoluene or alpha-tocopherol acetate, or chelators.

A typical formulation and lyophilization cycle useful in accordance with the present invention is provided below. Lyophilization can be carried out using standard equipment as used for lyophilization or vacuum drying. The cycle may be varied depending upon the equipment and facilities used for the fill/finish.

In accordance with a typical embodiment of the present invention, an aqueous pre-lyophilization solution or dispersion is first formulated in a pharmaceutically acceptable compounding vessel. The solution is aseptically filtered into a sterile container, filled into an appropriate sized vial, partially stoppered and loaded into the lyophilizer. Using lyophilization techniques described herein the solution is lyophilized until a moisture content in the range of about 0.1 to about 8.0 percent is achieved. The resulting lyophilization powder is stable as a lyophilized powder for about six months to greater than about 2 years, preferably greater than about 3 years at about 5° C. to about 25° C. and can be readily reconstituted with Sterile Water for Injection, or other suitable carrier, to provide liquid formulations of bendamustine, suitable for internal administration e.g., by parenteral injection. For intravenous administration, the reconstituted liquid formulation, i.e., the pharmaceutical composition, is preferably a solution.

The pre-lyophilization solution or dispersion normally is first formulated in a pharmaceutically acceptable container by: 1) adding an excipient, such as mannitol (about 0 to about 50 mg/mL) with mixing to water (about 65% of the total volume) at ambient temperature, 2) adding an organic solvent (0.5-99.9% v/v), such as TBA to the aqueous solution with mixing at about 20°-35° C., 4) adding bendamustine HCl to the desired concentration with mixing, 5) adding water to achieve the final volume, and 6) cooling the solution to about 1° C. to about 30° C., preferably about 5° C. Although the preceding steps are shown in a certain order, it is understood that one skilled in the art can change the order of the steps and quantities as needed. Quantities can be prepared on a weight basis also.

The pre-lyophilization solution or dispersion can be sterilized prior to lyophilization, sterilization is generally performed by aseptic filtration, e.g., through a 0.22 micron or less filter. Multiple sterilization filters can be used. Sterilization of the solution or dispersion can be achieved by other methods known in the art, e.g., radiation.

In this case, after sterilization, the solution or dispersion is ready for lyophilization. Generally, the filtered solution will be introduced into a sterile receiving vessel, and then transferred to any suitable container or containers in which the formulation may be effectively lyophilized. Usually the formulation is effectively and efficiently lyophilized in the containers in which the product is to be marketed, such as, without limitation, a vial, as described herein and as known in the art.

A typical procedure for use in lyophilizing the pre-lyophilization solutions or dispersions is set forth below. However, a person skilled in the art would understand that modifications to the procedure or process may be made depending on such things as, but not limited to, the pre-lyophilization solution or dispersion and lyophilization equipment.

Initially, the product is placed in a lyophilization chamber under a range of temperatures and then subjected to temperatures well below the product's freezing point, generally for several hours. Preferably, the temperature will be at or below about −40° C. for at least 2 hours. After freezing is complete, the chamber and the condenser are evacuated through vacuum pumps, the condenser surface having been previously chilled by circulating refrigerant. Preferably, the condenser will have been chilled below the freezing point of the solution preferably to about −40°, more preferably to about −50° C. or lower, even more preferably to about −60° C. or lower. Additionally, evacuation of the chamber should continue until a pressure of about 10 to about 600 microns, preferably about 50 to about 150 microns is obtained.

The product composition is then warmed under vacuum in the chamber and condenser. This usually will be carried out by warming the shelves within the lyophilizer on which the product rests during the lyophilization process at a pressure ranging from about 10 to about 600 microns. The warming process will optimally take place very gradually, over the course of several hours. For example, the product temperature should initially be increased from about −30° C. to about −10° C. and maintained for about 10-70 hours. Additionally, the product temperature can be increased from the freezing temperature to about 25° C.-40° C. over a period of 30-192 hours. To prevent powder ejection of the lyophilate from vials, complete removal of the organic solvent and water should be done during the initial drying phase. Complete drying can be confirmed by stabilization of vacuum, condenser temperature and product shelf temperature. After the initial drying, the product temperature should be increased to about 25° C.-40° C. and maintained for about 5-40 hours.

Once the drying cycle is completed, the pressure in the chamber can be slowly released to atmospheric pressure (or slightly below) with sterile, dry-nitrogen gas (or equivalent gas). If the product composition has been lyophilized in containers such as vials, the vials can be stoppered, removed and sealed. Several representative samples can be removed for purposes of performing various physical, chemical, and microbiological tests to analyze the quality of the product.

The lyophilized bendamustine formulation is typically marketed in pharmaceutical dosage form. The pharmaceutical dosage form of the present invention, although typically in the form of a vial, may be any suitable container, such as ampoules, syringes, co-vials, which are capable of maintaining a sterile environment. Such containers can be glass or plastic, provided that the material does not interact with the bendamustine formulation. The closure is typically a stopper, most typically a sterile rubber stopper, preferably a bromobutyl rubber stopper, which affords a hermetic seal.

After lyophilization, the bendamustine lyophilization powder may be filled into containers, such as vials, or alternatively the pre-lyophilization solution can be filled into such vials and lyophilized therein, resulting in vials which directly contain the lyophilized bendamustine formulation. Such vials are, after filling or lyophilization of the solution therein, sealed, as with a stopper, to provide a sealed, sterile, pharmaceutical dosage form. Typically, a vial will contain a lyophilized powder including about 10-500 mg/vial, preferably about 100 mg/vial, bendamustine and about 5 mg-2 g/vial, preferably about 170 mg/vial, mannitol.

The lyophilized formulations of the present invention may be reconstituted with water, preferably Sterile Water for Injection, or other sterile fluid such as co-solvents, to provide an appropriate solution of bendamustine for administration, as through parenteral injection following further dilution into an appropriate intravenous admixture container, for example, normal saline.

B. Solubility

The solubility of bendamustine HCl (bendamustine) in water (alone) and with varying amounts of alcohols commonly used in lyophilization, e.g., methanol, ethanol, propanol, isopropanol, butanol and tertiary-butyl alcohol (TBA) was determined by visual inspection. Amounts of bendamustine at 15 mg/mL, combined with mannitol at 25.5 mg/mL were prepared in 10 mL of the indicated alcohol solutions at room temperature (see Table 1). Samples were then refrigerated at 5° C. and inspected after 0, 3, 6 and 24 hours for particulates and/or precipitates.

The results shown in Table 1 indicate that bendamustine solubility is dependant on temperature and the amount of alcohol in aqueous solutions. For the alcohols tested, the solubility of bendamustine increased as the concentration of alcohol increased. The formation of a precipitant was also dependent on the temperature and time. Bendamustine did not precipitate immediately with any alcohol, but crystallized after storage at 5° C. Alcohols varied in their effect on solubility. Without wishing to be bound to any particular theory, smaller alcohols such as methanol and ethanol have less of an effect on solubility as compared with larger alcohols (tertiary-butanol and n-butanol). However, the shape of the alcohol is also important. For example n-propanol was found to be better than iso-propanol in preventing precipitation in this system. The two alcohols with the greatest effect on solubility were n-propanol and tertiary-butanol.

TABLE 1

Bendamustine solubility over a 24 hour period in various alcohols when stored at 5° C.

|  | Zero Time | 3 Hours | 6 Hours | 24 Hours |
|---|---|---|---|---|
| Methanol (v/v) |  |  |  |  |
| 0% (Water Only) | CCS | CCS | Precipitate | Precipitate |
| 5% | CCS | CCS | Precipitate | Precipitate |
| 10% | CCS | CCS | CCS | Precipitate |
| 20% | CCS | CCS | CCS | Precipitate |
| 30% | CCS | CCS | CCS | CCS |
| Ethanol (v/v) |  |  |  |  |
| 1.9% | CCS | CCS | Precipitate | Precipitate |
| 5% | CCS | CCS | Precipitate | Precipitate |
| 10% | CCS | CCS | CCS | Precipitate |
| 20% | CCS | CCS | CCS | CCS |
| 30% | CCS | CCS | CCS | CCS |
| n-Propanol (v/v/) |  |  |  |  |
| 5% | CCS | CCS | CCS | Precipitate |
| 10% | CCS | CCS | CCS | CCS |
| 20% | CCS | CCS | CCS | CCS |
| 30% | CCS | CCS | CCS | CCS |
| Iso-propanol (v/v) |  |  |  |  |
| 5% | CCS | Precipitate | Precipitate | Precipitate |
| 10% | CCS | CCS | CCS | CCS |
| 20% | CCS | CCS | CCS | CCS |
| 30% | CCS | CCS | CCS | CCS |
| n-Butanol (v/v) |  |  |  |  |
| 5% | CCS | CCS | CCS | CCS |
| 10% | CCS | CCS | CCS | CCS |
| 20% | 2 layers | 2 layers | 2 layers | 2 layers |
| 30% | 2 layers | 2 layers | 2 layers | 2 layers |
| Tert-Butanol (v/v) |  |  |  |  |
| 5% | CCS | CCS | CCS | Precipitate |
| 10% | CCS | CCS | CCS | Precipitate |
| 20% | CCS | CCS | CCS | CCS |
| 30% | CCS | CCS | CCS | CCS |

CCS stands for clear colorless solution

Experiments to quantitatively determine the solubility of bendamustine at various temperatures for three different solutions are summarized in FIG. 1 and Table 2. The amount of TBA, 20% (v/v) and 30% (v/v), used in the experiment was based on stability studies (results described below). For both solutions tested, the solubility of bendamustine decreased linearly with temperatures from 25° C. to 0° C. This experiment confirmed the data shown in Table 1 and highlights the difference in bendamustine solubility for 20% and 30% TBA solutions.

TABLE 2

Solubility of bendamustine in TBA

|  | −8° C. | 0° C. | 5° C. | 25° C. |
|---|---|---|---|---|
| 20% (v/v) TBA |  |  |  |  |
| 25.5 mg/mL mannitol Water, q.s. to desired volume | 14 mg/mL | 11 mg/mL | 17 mg/mL | 47 mg/mL |
| 30% (v/v) TBA |  |  |  |  |
| 25.5 mg/mL mannitol Water, q.s. to desired volume | 20 mg/mL | 18 mg/mL | 27 mg/mL | 65 mg/mL |

C. Stability

Because of its instability in aqueous solutions due to hydrolysis with water, bendamustine requires lyophilization in order to make a product suitable for pharmaceutical use. However, during the manufacturing of lyophilized drug products, aqueous solutions are commonly needed for filling, prior to lyophilization. Thus, the use of aqueous solutions during the compounding and fill processes for bendamustine and other nitrogen mustards can result in degradation of the drug product. Consequently, the effect of various alcohols on the degradation of bendamustine was evaluated to determine if formulations could be found that would allow longer fill-finish times, provide lyophilate powders that could be reconstituted more quickly than the current Ribomustin® formulation, and/or provide lyophilized preparations of bendamustine with a better impurity profile with respect to certain impurities, e.g., HP1, and BM1 dimer than Ribomustin®.

Preferably, a lyophilized preparation of the invention is stable with respect to HP1, i.e., the amount of HP1 does not increase appreciably (does not exceed the shelf-life specifications), for 6 months, more preferably 12 months, and even more preferably greater than 24 months, e.g., 36 months, when stored at about 2° C. to about 30° C., preferably 5° C.

Table 3 shows the stability results of bendamustine in water with no addition of alcohol over a 24 hour period at 5° C. Bendamustine degrades rapidly in water alone and forms predominantly the hydrolysis product, HP1 (monohydroxy bendamustine).

Formula II

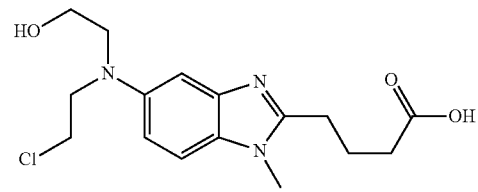

Monohydroxy bendamustine (HP1)

TABLE 3

Stability of bendamustine in water

|  | Hold Time | Purity (% Area) | HP1 (%) | Dimer (%) |
|---|---|---|---|---|
| 0% Alcohol, i.e., Water Alone | 0 hours | 99.11 | 0.60 | 0.11 |
|  | 3 hours | 98.83 | 0.86 | 0.13 |
|  | 6 hours | 98.44 | 1.22 | 0.17 |
|  | 24 hours | 95.67 | 3.81 | 0.29 |

The other major degradant observed during this study and other long term stability studies was the dimer of bendamustine.

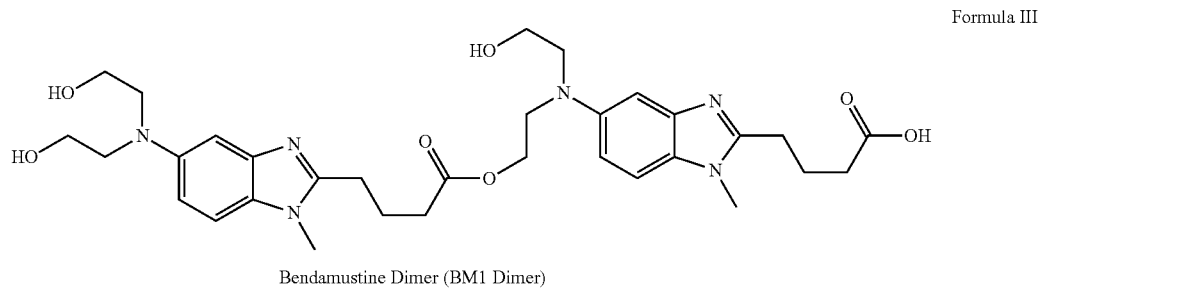 [SMILES: Cn1c(CCCC(=O)O)nc2cc(N(CCO)CCOC(=O)CCCc3nc4cc(N(CCO)CCO)ccc4n3C)ccc21]

Bendamustine Dimer (BM1 Dimer)

Formula III

Other degradants contained in the Ribomustin lyophilized product are bendamustine ethylester (BM1EE) (Formula IV) and BM1DCE (Formula V). BM1EE is formed when bendamustine reacts with ethyl alcohol.

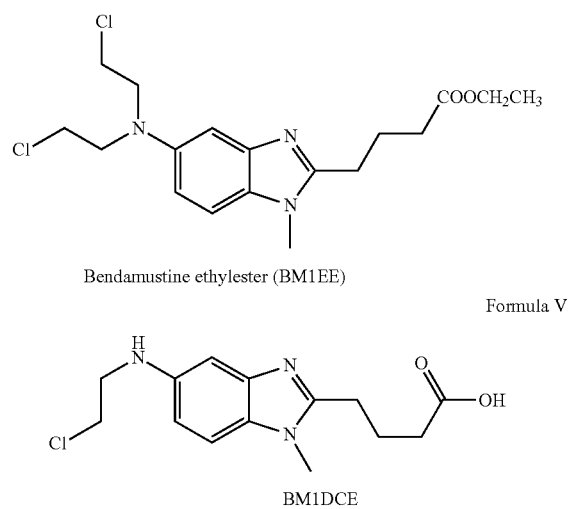

Bendamustine ethylester (BM1EE)

Formula IV

BM1DCE

Formula V

Figure 2:
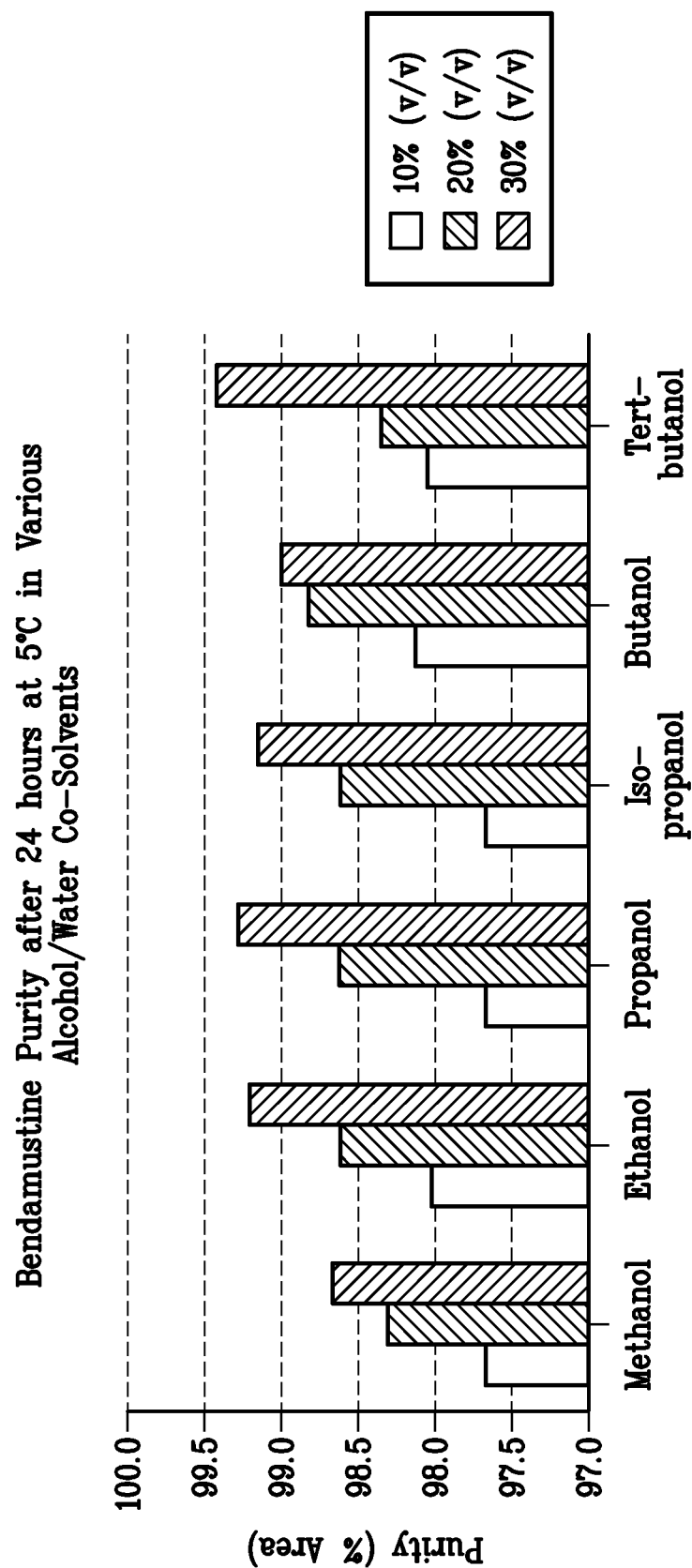
FIG. 2 shows the purity results of an HPLC analysis after incubating bendamustine in various alcohols for 24 hours at 5° C. Results are presented as the area percent of the bendamustine peak.

FIG. 2 summarizes the purity results of an HPLC analysis after incubating bendamustine in various alcohols for 24 hours at 5° C. Results are presented as the area percent of the total peak area. The numerical values for FIG. 2 are provided in Tables 3-9. The purity was highest in solutions containing higher concentration of alcohols, regardless of the alcohol. Of the alcohols evaluated, bendamustine degraded the least in a solution containing about 30% (v/v) TBA. In about 10% and about 20% alcohol solutions, n-butanol was superior in preventing degradation of bendamustine. At 20% and 30% (v/v), n-butanol in water resulted in a biphasic system due to the insolubility of n-butanol in water at these concentrations.

Figure 3:
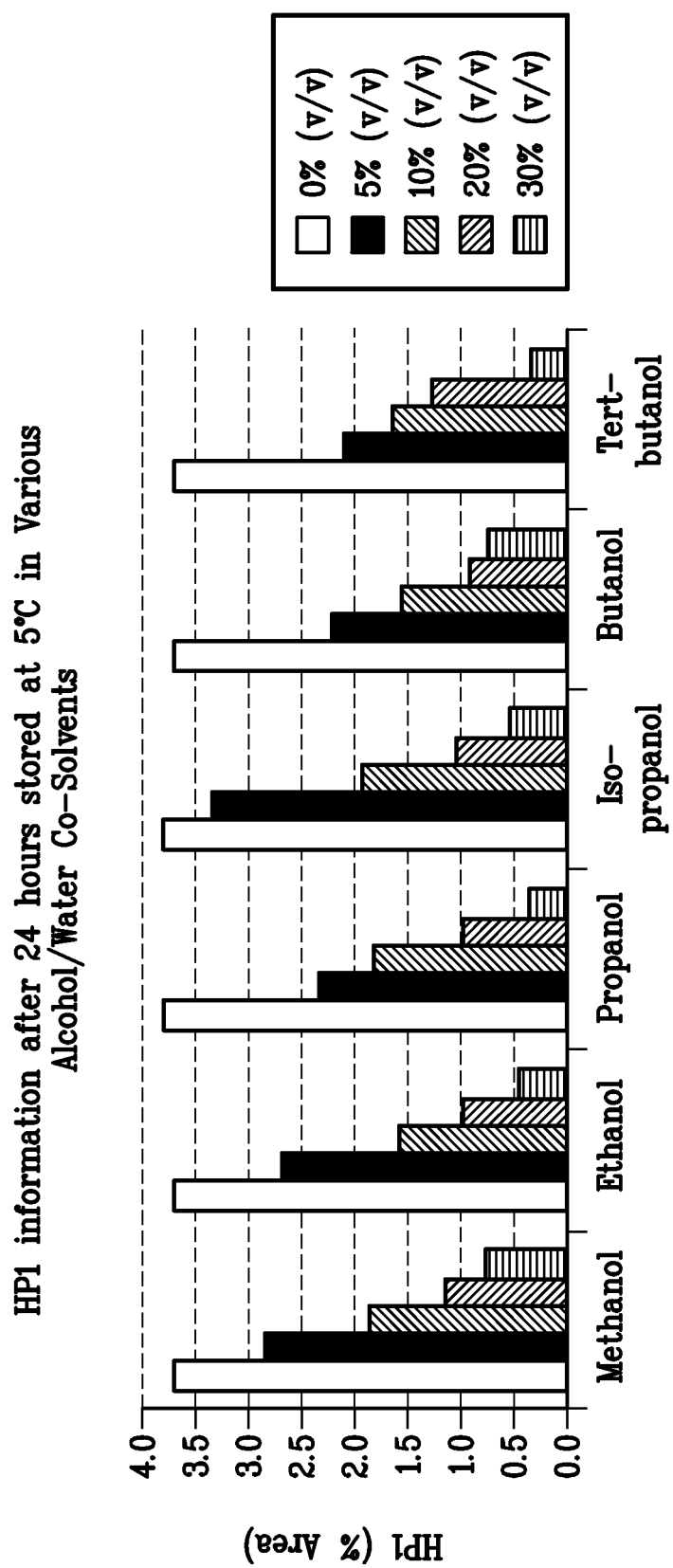
FIG. 3 shows HP1 (Formula II) formation after 24 hours in various alcohol/water co-solvents at 5° C.
Figure 4:
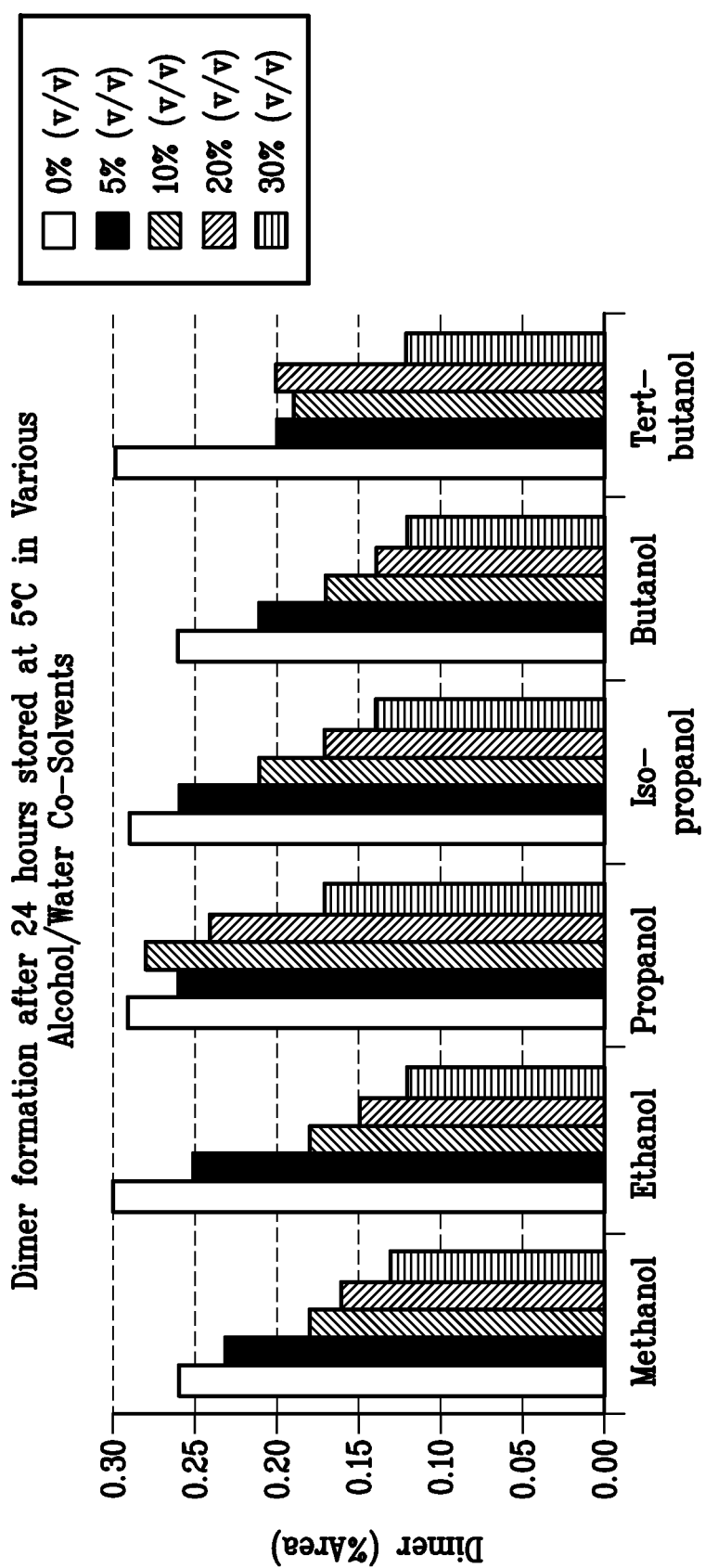
FIG. 4 shows dimer (Formula III) formation after 24 hours in various alcohol/water co-solvents at 5° C.

FIGS. 3 and 4 show the amount of degradation of bendamustine as measured by HP1 and dimer formation quantified by HPLC (as described herein). HP1 and dimer formation increased as the amount of alcohol concentration decreased regardless of the alcohol. This increase in impurities occurred with an anticipated time dependence (see Tables 3-9). Tert-butanol and n-butanol appeared superior to other alcohols in preventing degradation of the product. As seen in Table 10, mannitol had no effect on the stabilization of bendamustine with TBA.

TABLE 4

HPLC stability results for the stability of bendamustine in various ethyl alcohol concentrations over a 24 hour period. HP1 and Dimer were impurities that increased in this study.

| V/V alcohol | Hold Time | Purity (% Area) | HP1 (%) | Dimer (%) |
|---|---|---|---|---|
| 1.9% Ethanol | 0 hours | 99.11 | 0.64 | 0.12 |
| | 3 hours | 98.83 | 0.90 | 0.14 |
| | 6 hours | 98.60 | 1.12 | 0.15 |
| | 24 hours | 96.16 | 3.41 | 0.27 |
| 5% Ethanol | 0 hours | 99.31 | 0.44 | 0.12 |
| | 3 hours | 99.10 | 0.64 | 0.13 |
| | 6 hours | 98.87 | 0.86 | 0.14 |
| | 24 hours | 96.89 | 2.68 | 0.25 |
| 10% Ethanol | 0 hours | 99.44 | 0.33 | 0.11 |
| | 3 hours | 99.28 | 0.48 | 0.12 |
| | 6 hours | 99.10 | 0.65 | 0.12 |
| | 24 hours | 98.03 | 1.57 | 0.18 |
| 20% Ethanol | 0 hours | 99.54 | 0.22 | 0.10 |
| | 3 hours | 99.45 | 0.30 | 0.11 |
| | 6 hours | 99.36 | 0.39 | 0.11 |
| | 24 hours | 98.61 | 0.96 | 0.15 |
| 30% Ethanol | 0 hours | 99.62 | 0.15 | 0.10 |
| | 3 hours | 99.56 | 0.21 | 0.11 |
| | 6 hours | 99.52 | 0.24 | 0.12 |
| | 24 hours | 99.21 | 0.45 | 0.12 |

TABLE 5

HPLC stability results for bendamustine in various Tert-butanol concentrations over a 24 hour period. HP1 and Dimer were impurities that increased in this study.

| Concentration alcohol (v/v) | Hold Time | Purity (% Area) | HP1 (%) | Dimer (%) |
|---|---|---|---|---|
| 5% Tert-butanol | 0 hours | 99.34 | 0.41 | 0.12 |
| | 3 hours | 99.10 | 0.64 | 0.14 |
| | 6 hours | 98.85 | 0.88 | 0.13 |
| | 24 hours | 97.58 | 2.09 | 0.20 |
| 10% Tert-butanol | 0 hours | 99.46 | 0.30 | 0.11 |
| | 3 hours | 99.26 | 0.48 | 0.12 |
| | 6 hours | 99.05 | 0.69 | 0.13 |
| | 24 hours | 98.04 | 1.64 | 0.19 |
| 20% Tert-butanol | 0 hours | 99.59 | 0.17 | 0.11 |
| | 3 hours | 99.48 | 0.29 | 0.11 |
| | 6 hours | 99.35 | 0.40 | 0.12 |
| | 24 hours | 98.35 | 1.27 | 0.20 |
| 30% Tert-butanol | 0 hours | 99.63 | 0.13 | 0.10 |
| | 3 hours | 99.60 | 0.16 | 0.10 |
| | 6 hours | 99.58 | 0.18 | 0.11 |
| | 24 hours | 99.42 | 0.34 | 0.12 |

TABLE 6

HPLC stability results for various n-propyl alcohol concentrations over a 24 hour period. HP1 and Dimer were impurities that increased in this study.

| Concentration alcohol (v/v) | Hold Time | Purity (% Area) | HP1 (%) | Dimer (%) |
|---|---|---|---|---|
| 5% n-Propanol | 0 hours | 99.25 | 0.43 | 0.13 |
| | 3 hours | 99.00 | 0.66 | 0.15 |
| | 6 hours | 98.72 | 0.94 | 0.16 |
| | 24 hours | 97.24 | 2.33 | 0.26 |
| 10% n-Propanol | 0 hours | 99.34 | 0.33 | 0.15 |
| | 3 hours | 99.17 | 0.48 | 0.14 |
| | 6 hours | 98.92 | 0.70 | 0.16 |
| | 24 hours | 97.67 | 1.83 | 0.28 |
| 20% n-Propanol | 0 hours | 99.45 | 0.33 | 0.13 |
| | 3 hours | 99.42 | 0.26 | 0.13 |
| | 6 hours | 99.29 | 0.39 | 0.14 |
| | 24 hours | 98.60 | 0.97 | 0.24 |
| 30% n-Propanol | 0 hours | 99.53 | 0.15 | 0.13 |
| | 3 hours | 99.51 | 0.15 | 0.15 |
| | 6 hours | 99.44 | 0.20 | 0.11 |
| | 24 hours | 99.27 | 0.36 | 0.17 |

TABLE 7

HPLC stability results for bendamustine in various iso-propyl alcohol concentrations over a 24 hour period. HP1 and Dimer were impurities that increased in this study.

| Concentration alcohol (v/v) | Hold Time | Purity (% Area) | HP1 (%) | Dimer (%) |
|---|---|---|---|---|
| 5% Iso-propanol | 0 hours | 99.21 | 0.48 | 0.13 |
| | 3 hours | 98.65 | 0.72 | 0.14 |
| | 6 hours | 98.56 | 1.02 | 0.14 |
| | 24 hours | 96.14 | 3.35 | 0.26 |
| 10% Iso-propanol | 0 hours | 99.32 | 0.37 | 0.12 |
| | 3 hours | 99.11 | 0.55 | 0.14 |
| | 6 hours | 98.85 | 0.75 | 0.16 |
| | 24 hours | 97.68 | 1.92 | 0.21 |
| 20% Iso-propanol | 0 hours | 99.49 | 0.21 | 0.11 |
| | 3 hours | 99.39 | 0.31 | 0.12 |
| | 6 hours | 99.22 | 0.42 | 0.13 |
| | 24 hours | 98.61 | 1.04 | 0.17 |
| 30% Iso-propanol | 0 hours | 99.56 | 0.15 | 0.10 |
| | 3 hours | 99.47 | 0.20 | 0.12 |
| | 6 hours | 99.40 | 0.24 | 0.11 |
| | 24 hours | 99.15 | 0.52 | 0.14 |

TABLE 8

HPLC stability results for bendamustine in various methyl alcohol concentrations over a 24 hour period. HP1 and Dimer were impurities that increased in this study.

| Concentration alcohol (v/v) | Hold Time | Purity (% Area) | HP1 (%) | Dimer (%) |
|---|---|---|---|---|
| 5% Methanol | 0 hours | 99.35 | 0.40 | 0.12 |
| | 3 hours | 98.97 | 0.70 | 0.14 |
| | 6 hours | 98.66 | 0.95 | 0.14 |
| | 24 hours | 96.65 | 2.83 | 0.23 |
| 10% Methanol | 0 hours | 99.42 | 0.34 | 0.11 |
| | 3 hours | 99.01 | 0.59 | 0.12 |
| | 6 hours | 98.86 | 0.80 | 0.12 |
| | 24 hours | 97.65 | 1.85 | 0.18 |
| 20% Methanol | 0 hours | 99.56 | 0.22 | 0.11 |
| | 3 hours | 99.31 | 0.38 | 0.11 |
| | 6 hours | 98.99 | 0.50 | 0.12 |
| | 24 hours | 98.31 | 1.15 | 0.16 |
| 30% Methanol | 0 hours | 99.59 | 0.18 | 0.10 |
| | 3 hours | 99.43 | 0.27 | 0.11 |
| | 6 hours | 99.25 | 0.34 | 0.11 |
| | 24 hours | 98.65 | 0.76 | 0.13 |

TABLE 9

HPLC stability results for bendamustine in various n-butyl alcohol concentrations over a 24 hour period. HP1 and Dimer were impurities that increased in this study.

| Concentration alcohol (v/v) | Hold Time | Purity (% Area) | HP1 (%) | Dimer (%) |
|---|---|---|---|---|
| 5% Butanol | 0 hours | 99.25 | 0.49 | 0.13 |
| | 3 hours | 98.94 | 0.73 | 0.14 |
| | 6 hours | 98.76 | 0.91 | 0.14 |
| | 24 hours | 97.46 | 2.20 | 0.21 |
| 10% Butanol | 0 hours | 99.44 | 0.30 | 0.11 |
| | 3 hours | 99.18 | 0.49 | 0.12 |
| | 6 hours | 99.03 | 0.64 | 0.12 |
| | 24 hours | 98.13 | 1.55 | 0.17 |
| 20% Butanol[a] | 0 hours | 99.54 | 0.23 | 0.10 |
| | 3 hours | 99.45 | 0.31 | 0.11 |
| | 6 hours | 99.30 | 0.40 | 0.11 |
| | 24 hours | 98.81 | 0.91 | 0.14 |
| 30% Butanol[a] | 0 hours | 99.55 | 0.24 | 0.10 |
| | 3 hours | 99.40 | 0.29 | 0.10 |
| | 6 hours | 99.40 | 0.37 | 0.11 |
| | 24 hours | 99.00 | 0.74 | 0.12 |

[a]Both solutions had 2 layers/phases of liquids in the vial. Solutions were vortexed prior to sample preparation.

The results in Tables 1-9 indicate that the stability of bendamustine HCl with respect to HP1 and dimer improves with increasing alcohol concentration.

TABLE 10

HPLC stability results for bendamustine in TBA with and without mannitol over a 24 hour period.

| Sample | Purity (% Area) | HP1 (%) |
|---|---|---|
| TBA 20% (v/v) with Mannitol | | |
| 0 hours | 99.59 | 0.17 |
| 24 hours @ 5° C. | 99.35 | 1.27 |
| TBA 20% (v/v) without Mannitol | | |
| 0 hours | 100.0 | 0.00 |
| 24 hours @ 5° C. | 98.80 | 1.21 |

NOTE:
The samples analyzed without mannitol were analyzed by HPLC using a normal phase method while the samples analyzed with mannitol used a reverse phase HPLC method. Slight variability may be seen in other samples analyzed between the two methods.

D. Lyophilization Cycle Development

Different pre-lyophilization formulations were prepared at various concentrations of bendamustine, mannitol, and alcohols in water. The cycle development was changed and optimized at each step for freezing (fast vs. slow), primary drying (both temperature and pressure), and secondary drying as described herein.

Based upon all of the information detailed above on solubility, stability, and ease of lyophilization, preferred formulations include the following:

| Ingredients | Concentration |
|---|---|
| Bendamustine | about 2-40 mg/mL |
| Mannitol | about 0-50 mg/mL |
| Alcohol | about 0.5%-40% (v/v) |
| Water, q.s. to | desired volume | wherein the alcohol is selected from methanol, n-propanol, or isopropanol

| Ingredients | Concentration |
|---|---|
| Bendamustine | about 5-20 mg/mL |
| Mannitol | 10-30 mg/mL |
| Alcohol | 1-20% (v/v) |
| Water, q.s. to | desired volume | wherein the alcohol is selected from methanol, n-propanol, or isopropanol

| Ingredients | Concentration |
|---|---|
| Bendamustine | about 5-20 mg/mL |
| Mannitol | 10-30 mg/mL |
| Alcohol | 5-40% (v/v) |
| Water, q.s. to | desired volume |

| Ingredients | Concentration |
|---|---|
| Bendamustine HCl | about 12-17 mg/mL |
| Mannitol | about 20-30 mg/mL |
| Alcohol | about 5-15% (v/v) |
| Water, q.s. to | desired volume |

| Ingredients | Concentration |
|---|---|
| Bendamustine HCl | about 15 mg/mL |
| Mannitol | about 25.5 mg/mL |
| Alcohol | about 10% (v/v) |
| Water, q.s. to | desired volume |

| Ingredients | Concentration |
|---|---|
| Bendamustine HCl | about 2-40 mg/mL |
| Mannitol | about 0-50 mg/mL |
| Butanol | about 0.5-20% (v/v) |
| Water, q.s. to | desired volume |

| Ingredients | Concentration |
|---|---|
| Bendamustine HCl | about 5-20 mg/mL |
| Mannitol | about 10-30 mg/mL |
| Butanol | about 1-10% (v/v) |
| Water, q.s. to | desired volume |

| Ingredients | Concentration |
|---|---|
| Bendamustine HCl | about 12-17 mg/mL |
| Mannitol | about 20-30 mg/mL |
| Butanol | about 1-10% (v/v) |
| Water, q.s. to | desired volume |

| Ingredients | Concentration |
|---|---|
| Bendamustine HCl | about 15 mg/mL |
| Mannitol | about 25.5 mg/mL |
| Butanol | about 10% (v/v) |
| Water, q.s. to | desired volume |

| Ingredients | Concentration |
|---|---|
| Bendamustine HCl | about 2-50 mg/mL |
| Mannitol | about 0-50 mg/mL |
| Tertiary butanol | about 0.5-100% (v/v) |
| Water, q.s. to | desired volume |

| Ingredients | Concentration |
|---|---|
| Bendamustine HCl | about 2-50 mg/mL |
| Mannitol | about 0-50 mg/mL |
| Tertiary butanol | about 0.5-99.9% (v/v) |
| Water, q.s. to | desired volume |

| Ingredients | Concentration |
|---|---|
| Bendamustine HCl | about 2-50 mg/mL |
| Mannitol | about 0-50 mg/mL |
| Tertiary butanol | about 0.5-99% (v/v) |
| Water, q.s. to | desired volume |

| Ingredients | Concentration |
|---|---|
| Bendamustine HCl | about 2-50 mg/mL |
| Mannitol | about 0-50 mg/mL |
| Tertiary butanol | about 90-99% (v/v) |
| Water, q.s. to | desired volume |

| Ingredients | Concentration |
|---|---|
| Bendamustine HCl | about 5-20 mg/mL |
| Mannitol | about 10-30 mg/mL |
| Tertiary butanol | about 5-80% (v/v) |
| Water, q.s. to | desired volume |

| Ingredients | Concentration |
|---|---|
| Bendamustine HCl | about 12-17 mg/mL |
| Mannitol | about 20-30 mg/mL |
| Tertiary butanol | about 10-50% (v/v) |
| Water, q.s. to | desired volume |

| Ingredients | Concentration |
| --- | --- |
| Bendamustine HCl | about 12.5-15 mg/mL |
| Mannitol | about 0-30 mg/mL |
| Ethanol | about 20-30% (v/v) |
| Water, q.s. to | desired volume |

| Ingredients | Concentration |
| --- | --- |
| Bendamustine HCl | about 15 mg/mL |
| Mannitol | about 25.5 mg/mL |
| Tertiary butanol | about 30% (v/v) |
| Water, q.s. to | desired volume |

EXAMPLES

The following Examples are provided to illustrate certain aspects of the present invention and to aid those of skill in the art in practicing the invention. These Examples are in no way to be considered to limit the scope of the invention in any manner.

Materials:
Bendamustine HCl, (Degussa, Lot #s 0206005 and 0206007)
Mannitol, NF or equivalent (Mallinckrodt)
Ethyl Alcohol Dehydrated (200 proof), USP or equivalent (Spectrum)
Tertiary-butyl alcohol, ACS (EM Science)
Methanol (Spectrum and EMD)
Propanol (Spectrum)
Iso-propanol (Spectrum)
Butanol (Spectrum)
Water, HPLC grade or equivalent (EMD)
Acetonitrile, HPLC grade or equivalent (EMD)
Trifluoroacetic Acid, J. T. Baker
Methanol, HPLC grade or equivalent (EM Science, Cat # MX0488P-1)
Trifluoroacetic Acid, HPLC grade or equivalent (JT Baker, Cat# JT9470-01)
Equipment:
Waters 2695 Alliance HPLC system with photodiode array detector
Waters 2795 Alliance HPLC system with dual wavelength detector
Analytical Balance (Mettler AG285, ID #1028) and (Mettler XS205)
VirTis Lyophilizer AdVantage
Agilent Zorbax SB-C18 5 μm 80 Å 4.6×250 mm column, Cat#880975-902

Example 1

HPLC Procedures

Method 1
Mobile Phase A: 0.1% TFA; $H_2O$
Mobile Phase B: 0.1% TFA; 50% ACN:50% $H_2O$
UV: 230 nm
Flow rate: 1.0 mL/min
Column temp.: 30° C.
Column: Zorbax SB-C18 5 μm 80 Å 4.6×250 mm
Sample temp.: 5° C.
Injection Volume: 10 μL
Sample Concentration: 0.25 mg/mL in MeOH
Gradient: 20% B for 1 min
　　20-90% B in 23 min
　　90% B for 6 min
　　back to 20% B in 1 min
　　hold at 20% B for 4 min
Run time: 30 min
Post run time: 5 min
Method 2
Mobile Phase A: 0.1% TFA; $H_2O$:ACN (9:1)
Mobile Phase B: 0.1% TFA; $H_2O$:ACN (5:5)
UV: 230 nm
Flow rate: 1.0 mL/min
Column: Zorbax SB-C18 5 μm 80 Å 4.6×250 mm
Column temp.: 30° C.
Sample temp.: 5° C.
Injection Volume: 10 μL
Sample Concentration: 0.25 mg/mL in MeOH
Gradient: 0% B for 3 min
　　0-50% B in 13 min
　　50-70% B in 17 min
　　70-90% B in 2 min
　　90% B for 5 min
　　back to 0% B in 1 min
　　hold at 0% B for 4 min
Run time: 40 min
Post run time: 5 min
Method 3
Phase A: HPLC grade water with 0.1% TFA(v/v)
Phase B: HPLC grade ACN/water(1:1 v/v) with 0.1% TFA (v/v)
UV: 254 nm
Flow rate: 1.0 mL/min
Column: Zorbax SB-C18 5 μm 80 Å 4.6×250 mm
Column temp.: 30° C.
Sample temp.: 5° C.
Injection Volume: 5 μL
Acquisition time: 30 min
Post time: 9 min
Diluent: methanol
Gradient:

| Time (min.) | % Phase A | % Phase B |
| --- | --- | --- |
| 0.0 | 82 | 18 |
| 7.0 | 60 | 40 |
| 11.0 | 60 | 40 |
| 15.0 | 20 | 80 |
| 30.0 | 20 | 80 |
| 31.0 | 82 | 18 |

Sample preparation—dissolve the drug product with 200 mL MeOH. Sonicate 6 minutes. The solution can be injected directly into the HPLC (ca. 0.5 mg/mL)

Method 4
Phase A: HPLC grade water with 0.1% TFA(v/v)
Phase B: HPLC grade ACN with 0.1% TFA(v/v)
UV: 254 nm
Flow rate: 1.0 mL/min
Column: Zorbax Bonus RP-C14 5 μm 4.6×150 mm
Column temp.: 30° C.
Sample temp.: 5° C.
Injection Volume: 2 μL
Acquisition time: 31 min
Post time: 5 min
Diluent: NMP/0.1% TFA in water (50:50 v/v)
Gradient:

| Time (min.) | % Phase A | % Phase B |
|---|---|---|
| 0.0 | 93 | 7 |
| 5 | 93 | 7 |
| 13 | 73 | 27 |
| 16 | 73 | 27 |
| 25 | 10 | 90 |
| 31 | 10 | 90 |

Sample preparation for method 4—dissolve the drug product with a known amount of diluent to prepare a concentration of 4.2 mg/mL for injection directly into the HPLC. It may be necessary to perform a second dilution (the 100 mg/vial dosage form) to obtain a 4.2 mg/mL sample concentration.

Results

Figure 6:
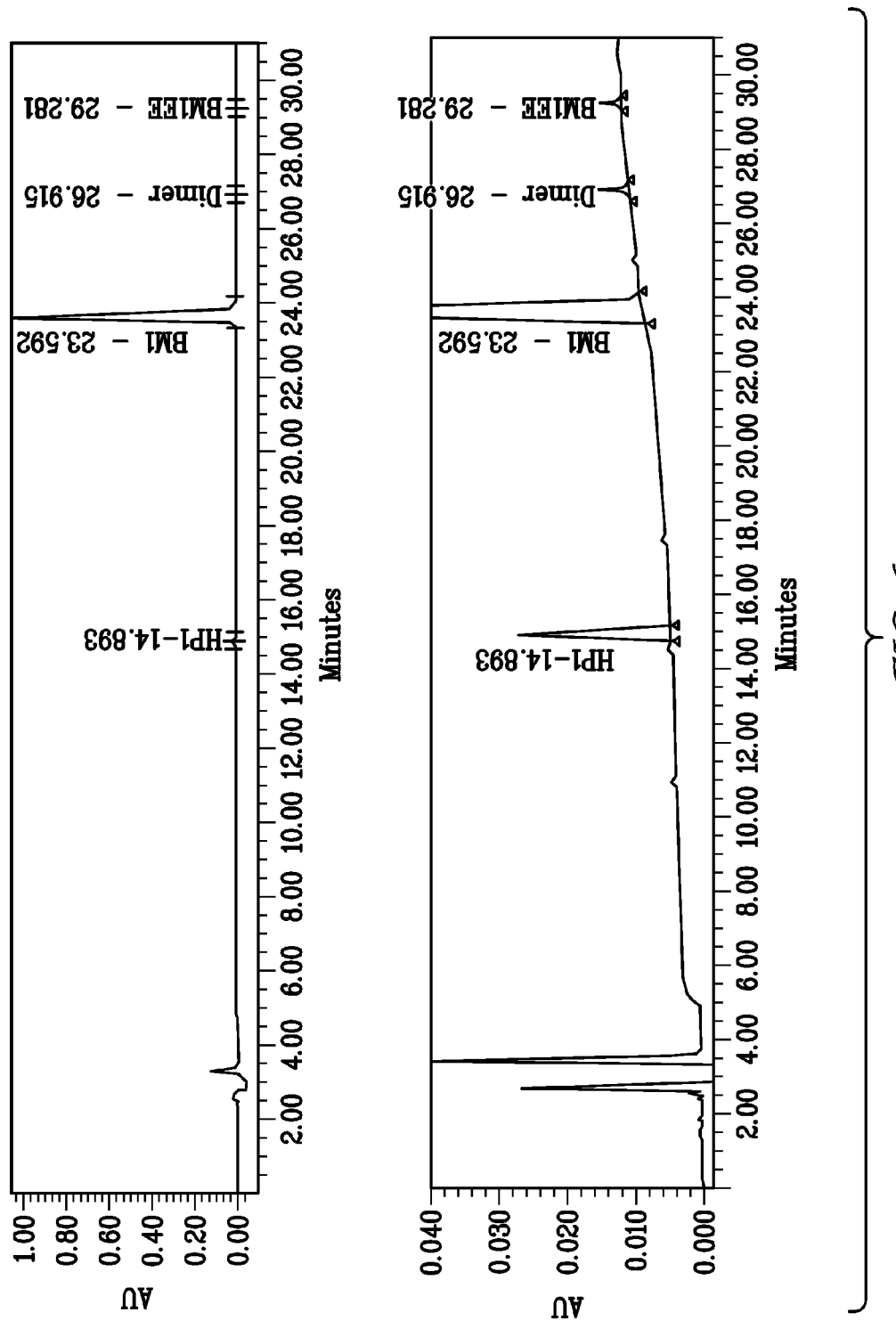
FIG. 6 shows a chromatogram for Ribomustin® using HPLC method No. 1.

The retention times for some Bendamustine impurities using HPLC Method 1 described above are shown in Table 11. An HPLC chromatograph for Ribomustin® using the HPLC procedure described herein is shown in FIG. 6.

TABLE 11

Retention Time for Bendamustine and some of its Impurities using HPLC Method 1

| Sample Name | Retention Time (min) |
|---|---|
| HP1 | 14.110 |
| Bendamustine | 22.182 |
| BM1 Dimer | 24.824 |
| BM1EE | 26.968 |

Although HPLC Method 1 was capable of resolving impurities found in bendamustine it was not capable of separating a potential impurity formed during analysis, the methyl ester of bendamustine (BM1ME). The retention time difference between BM1ME and BM1 Dimer was only 0.3 minutes. In order to resolve BM1 Dimer, another HPLC method (#2) was developed. HPLC method #2 was capable of separating all the impurities but required a longer run time of 45 minutes (Table 12).

TABLE 12

Retention Time for bendamustine and impurities using HPLC Method 2

| Sample Name | Retention Time (min) |
|---|---|
| HP1 | 15.694 |
| BM1 | 25.420 |
| BM1ME | 31.065 |
| BM1 Dimer | 32.467 |
| BM1EE | 36.038 |

The impurity profile of various lots of Ribomustin using HPLC Method 3 are shown in Table 13.

TABLE 13

Ribomustine Impuirty Profile using HPLC Method 3
% Area

| Batch | Bendamustine(HCl) | HP1 | BM1EE | BM1 Dimer | BM1DCE |
|---|---|---|---|---|---|
| 03H08 | 98.14 | 1.07 | 0.21 | 0.34 | 0.03 |
| 03H07 | 97.67 | 1.5 | 0.2 | 0.33 | 0.04 |
| 02K27 | 96.93 | 0.93 | 0.29 | 1.18 | 0.08 |
| 03C08 | 97.61 | 1.24 | 0.19 | 0.46 | 0.02 |

Example 2

Solubility

The solubility of bendamustine HCl (bendamustine) in water (alone) and with varying amounts of methanol, ethanol, propanol, isopropanol, butanol and tertiary-butyl alcohol (TBA) was determined by visual inspection. Amounts of bendamustine at 15 mg/mL, mannitol at 25.5 mg/mL were prepared in 10 mL of the indicated alcohol solutions (Table 1) at room temperature. Samples were then refrigerated at 5° C. and inspected after 0, 3, 6 and 24 hours for particulates and/or precipitates.

Results summarized in Table 1 indicate that bendamustine solubility is dependant on temperature and the amount of alcohol in aqueous solutions. For all alcohols the solubility of bendamustine increased as the concentration of alcohol increased. The formation of a precipitant was also dependent on the temperature and time.

The solubility of bendamustine was also determined in 20% (v/v) TBA containing 25.5 mg/mL mannitol in water, and 30% (v/v) TBA containing 25.5 mg/mL mannitol in water (FIG. 1). Bendamustine was added to 4 mL of each solution while mixing until it would no longer dissolve. The saturated solutions were allowed to mix for 1 hour at −8° C., 0° C., 5° C., or 25° C. The samples were centrifuged and placed back at the original temperature for a minimum of 30 minutes. The −8° C. sample was placed into an ice bath containing sodium chloride, which lowers the temperature of the ice bath, and the temperature was measured when the sample was pulled for analysis. An aliquot of each sample was taken and prepared for HPLC analysis.

The results of these experiments are shown in FIG. 1 and Table 2. The amount of TBA, 20% (v/v) and 30% (v/v), used in the experiment (FIG. 1) was based on stability studies described herein.

As indicated in FIG. 1, the solubility of bendamustine decreased linearly with temperature (25° C. to 0° C.). The solubility of bendamustine was temperature dependant whether it was dissolved in water alone or with an alcohol. The 20% (v/v) TBA may likely be the lower limit required for efficient and robust pharmaceutical manufacturing due to the stability and solubility of bendamustine. A filling solution of 15 mg/mL bendamustine is close to the saturation limit of 17.2 mg/mL bendamustine at 5° C. but higher than the limit at 0° C. The 30% (v/v) TBA is the recommended concentration of TBA for the final formulation and is well within the solubility limit regardless of temperature.

Example 3

Stability

A. Stability in Water
Solutions of bendamustine (15 mg/mL), and mannitol (25.5 mg/mL) were prepared in water at room temperature and immediately placed in an ice bath (to lower the temperature quickly to about 5° C.) for 10 minutes and then refrigerated at 5° C. A sample of each formulation was analyzed by HPLC using the methods described herein after 0, 3, 6 and 24 hours when stored at 5° C.

B. Stability in Alcohols

Solutions containing 15 mg/mL bendamustine, 25.5 mg/mL mannitol, and 1.9%, 5%, 10%, 20% or 30% (v/v) ethyl alcohol in water or 5%, 10%, 20% or 30% (v/v) TBA, methanol, propanol, iso-propanol, or butanol in water were prepared at room temperature, placed into an ice bath for 10 minutes and then refrigerated at 5° C. A sample of each formulation was analyzed by HPLC after 0, 3, 6 and 24 hours when stored at 5° C.

C. Stability Results

Table 3 shows the stability results of bendamustine in water with no addition of alcohol over a 24 hour period at 5° C. Bendamustine degrades quickly in water but the stability of bendamustine increases with increasing alcohol concentrations (FIGS. 2, 3 and 4). Although alcohols are frequently used in lyophilization to aid in solubility problems, the effect of alcohols on bendamustine stability is unique, unexpected and useful in manufacturing bendamustine with fewer impurities since an aqueous solution can be used while maintaining the stability of bendamustine. TBA was found to be the best stabilizer of the six alcohols tested (FIGS. 2, 3, and 4). All alcohols at 30% (v/v) reduced the formation of impurities HP1 and Dimer at 5° C. for up to 24 hours. With respect to TBA, HP1 reaches only about 0.4% when stored at 5° C. for up to 24 hours. Lower concentrations of alcohol may not be efficient, when formulated at 15 mg/mL bendamustine and stored at 5° C. due to bendamustine precipitation and impurity formation.

Example 4

Formulation Optimization

After the solubility and stability of bendamustine were determined, the formulation was optimized for lyophilization. Since the concentration of bendamustine is higher in a 30% TBA/water saturated solution as compared with other alcohol solutions, it is anticipated that the vial size required to fill 100 mg of bendamustine can be decreased from the current Ribomustin® presentation. Although a saturated solution of bendamustine contains 18 mg/mL at 0° C., a concentration of 15 mg/mL was selected for the formulation to compensate for slight differences in API solubility due to differences in bulk API purity as a result of batch differences. A concentration of 15 mg/mL bendamustine requires 6.67 mL to fill 100 mg of bendamustine HCl per vial.

The surface (sublimation) area to volume ratio is critical to producing a lyophilized product with good appearance that freeze dries quickly. Generally, lyophilized products occupy between 30% to 50% of the vial volume. A 20 mL vial with 6.67 mL contains about 30% of its capacity and has a surface area ratio of 0.796 cm$^2$/mL.

Mannitol was selected as the bulking agent in order to maintain a formulation similar to Ribomustin®. Studies were performed to evaluate the effect of mannitol on bendamustine solubility and appearance of the product. Mannitol decreases the solubility of bendamustine (at 15 mg/mL) in both ethanol and TBA aqueous solutions. For example, solutions containing 5% and 10% ethanol and TBA without mannitol did not precipitate over 24 hours. However, for samples with mannitol (Table 1) precipitate was observed within 24 hours. There was no precipitate with aqueous solutions containing 30% (v/v) TBA, 15 mg/mL bendamustine, and 25.5 mg/mL mannitol. In order to maintain a well formed cake resistant to breakage during handling, a minimum of 134 mg/vial of mannitol was required with no difference observed in vials up to 200 mg/vial of mannitol.

All alcohols tested increased the stability and solubility of bendamustine. However, a significant mole fraction was required to affect the stability of the filling solution and the ease of manufacturing. Smaller alcohols have the undesirable effect of lowering the freezing point of the bulk solution and thus requiring long lyophilization cycles at lower temperatures. Higher concentrations of methanol and ethanol produced unattractive cakes that were difficult to reconstitute. 10% ethanol, 20% ethanol, 10% iso-propanol, 20% iso-propanol, or 30% TBA aqueous solutions containing bendamustine (15 mg/mL), mannitol (25.5 mg/mL) were prepared and lyophilized. The lyophilized vials filled from solutions of 10% ethanol, 20% ethanol, 10% iso-propanol, 20% iso-propanol produced either a collapsed cake or a film residue. The only solvent system producing an acceptable cake was 30% TBA. Additionally, reconstitution of 10% ethanol, 20% ethanol, 10% iso-propanol, 20% iso-propanol lyophilized vials were difficult and did not fully dissolve until >45 minutes.

The ability to utilize a smaller vial is constrained by the concentration or solubility of bendamustine in the aqueous/organic solution. At lower concentrations of ethanol, methanol, isopropanol and n-propanol, which produced acceptable cake appearance, a more dilute solution of bendamustine is required due to solubility limitations. To maintain a presentation with 100 mg of bendamustine per vial, a vial larger than 50 mL would be required. Also, stability studies herein indicated that at the lower alcohol concentration, the chemical stability was not sufficient to allow for acceptable filling times.

One of the factors affecting the ease of reconstitution is the porosity of the lyophilate. In general, amorphously precipitated solids with little surface area are more difficult to solubilize. Most lyophilates containing mannitol will reconstitute within 3-5 minutes as long as there is no precipitate formed during lyophilization, frequently caused by evaporation of a liquid (melt back). Based on our experience with several lyophilization solvent systems and not wishing to be bound to any particular theory, the problems associated with Ribomustin® reconstitution may be associated with precipitation caused by melt back during lyophilization. Most organic solvents do not lyophilize efficiently and cause melt back because of their low melting point. TBA (tertiary butyl alcohol) has a high melting point and a similar vapor pressure as compared to water. TBA is removed by sublimation, not evaporation, at about the same rate as water. Lyophilates produced with 30% (v/v) TBA according to the invention reconstitute within 3-10 minutes as compare to commercially available Ribomustin which may take 30-45 minutes.

Based upon the solubility, stability, ease of reconstitution and manufacturing considerations, the following is a preferred pre-lyophilization formulation of the present invention: bendamustine HCl about 15 mg/mL, mannitol about 25.5 mg/mL, about 30% (v/v) tertiary-butyl alcohol, and q.s. using water for Injection. The formulation is then filled at 5° C. using 6.67 mL in an amber 20 mL, 20 mm vial and partially stoppered with a bromobutyl stopper and loaded into a pre-chilled lyophilizer.

Example 5

Impurity Assessment

Major impurities introduced during Ribomustin® manufacturing, compounding, fill, and lyophilization procedure, as determined by HPLC analysis (FIG. 6), are the hydrolysis product HP1, the Dimer, and the ethyl ester of bendamustine, BM1EE. BM1EE can be formed during drug substance manufacturing, e.g., during recrystallization and/or purification processes. BM1EE is known to be a more potent cytotoxic drug than bendamustine. Experiments were undertaken to determine if the use of a 30% TBA aqueous filling solution would lead to the formation of bendamustine t-butyl ester.

Experiments were performed using traditional Fisher esterfication reaction conditions required for the formation of t-butyl ester of bendamustine. Bendamustine was heated in 60° C. TBA with HCl for 20 hours. No reaction was observed. This result indicated that it would be very difficult to form the tert-butyl ester of bendamustine during the fill/finish process. No new impurities in drug product manufactured from TBA have been observed in stability studies to date.

To aid in the testing of the drug product, synthetic routes using more reactive sources of the t-butyl moiety were developed. Another attempt to make tert-butyl ester was carried out by formation of the acyl chloride of bendamustine. A suspension of bendamustine in methylene chloride was treated with oxalyl chloride and N,N-dimethylformamide. After acyl chloride was formed, the solvent was concentrated. The residue was added to methylene chloride, tert-butanol, triethylamine, and 4-dimethylaminopyridine and the mixture was stirred at room temperature overnight. After adding all solvents and purification, an unknown compound was given. The LC-MS did not match the molecular weight of bendamustine tert-butyl ester and the proton NMR did not showed the peak for tert-butyl. Therefore, this attempt also failed to produce the bendamustine tert-butyl ester. Thus, using TBA as the co-solvent has an additional benefit of not forming the ester from the alcohol.

Example 6

Lyophilization Cycle Development

Numerous lyophilization cycles were performed to evaluate the critical stages of lyophilization and achieve the most efficient drying cycle. Experiments were performed to evaluate the effect of the freezing rate, primary drying temperature, time, and pressure on the product.

A. Freezing Rate

The literature reports that TBA adopts different crystal forms depending on the freeze rate. In some TBA solutions, the slower the product froze, the quicker it dried. Larger crystals formed during slow freezing producing bigger pores allowing more efficient sublimation. However, during studies with bendamustine, the freezing rate was not found to be a critical processing parameter when evaluated at 2 and 8 hours.

B. Primary and Secondary Drying

During the first attempts to lyophilize from 30% TBA solutions, the lyophilized cake fractured and powder was ejected from the vial. These cakes appeared to contain amorphous particles within the lyophilate, an indication of melt back. This phenomenon was reproducible and occurred when the product reached about −10° C. (refer to FIG. 5) independent of the warming rate. Several variables were tested to determine the cause and solution to the problem of the powder ejection. The pressure was raised from 50 µm to 150 µm during primary drying, but powder ejection was still observed but to a lesser extent. This experiment was then repeated except the freezing rate was extended to 8 hours from 2 hours. This change had no effect.

Figure 5:
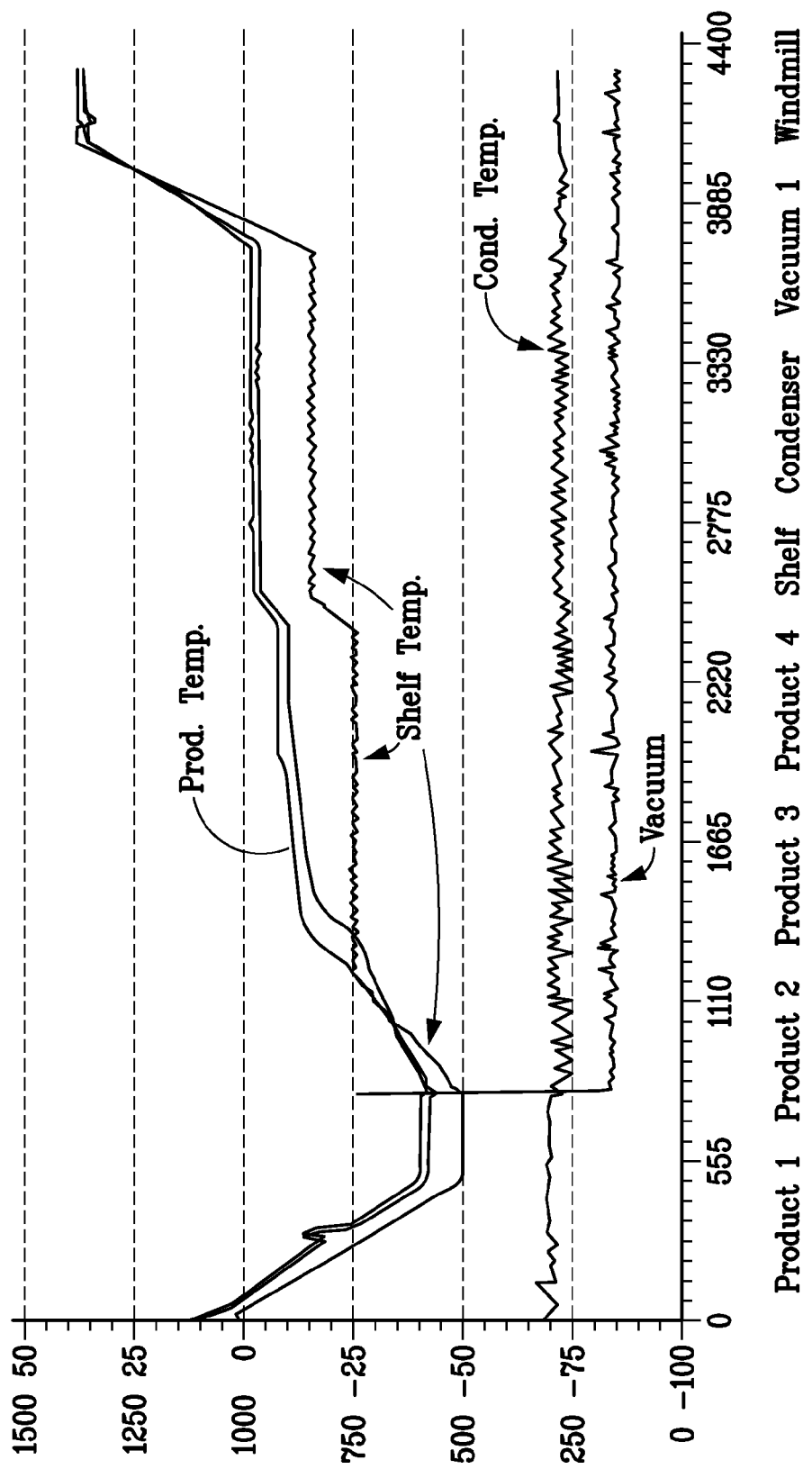
FIG. 5-shows a lyophilization cycle for bendamustine using a TBA/water co-solvent.

The length of primary drying was next evaluated. For example, the following very slow drying cycle was evaluated: freezing from +25° C. to −50° C. in eight hours; holding at −50° C. for 5 hours, warming and drying from −50° C. to −25° C. in seven hours; holding for twenty hours at −25° C., warming and drying from −25° C. to −15° C. in two hours and holding for twenty hours at −15° C., warming and drying from −15° C. to 40° C. in six hours and holding for twenty hours at 40° C. while maintaining a chamber pressure of 150 µm throughout drying. No powder ejection (FIG. 5) was observed. This cycle resulted in a well-formed cake without fracture that reconstituted readily. Without wishing to be bound to a particular theory, the problems with powder ejection and difficulty with reconstitution may be the result of drying the lyophilate too quickly, thus resulting in strong vapor flow out of the cake as well as melt back. With the use of a less aggressive drying cycle an aesthetic, stable, and easy to reconstitute cake was reproducibly formed. Thus, removing all unbound water and tertiary-butyl alcohol prior to secondary drying may prevent melt back as well as powder ejection. The lyophilization cycle was further optimized under these gentle conditions (FIG. 5). There were no immediate degradation products as a result of drying at 40° C. for up to 20 hours.

Example 7

Lyophilization Cycle

| Step | Description | Time (Hour) | Temperature (° C.) | Pressure (Microns) |
|---|---|---|---|---|
| 1 | Hold | 0.25 | 5° C. | — |
| 2 | Ramp | 8 | −50° C. | — |
| 3 | Hold | 4 | −50° C. | — |
| 4 | Ramp | 3 | −20° C. | 150 |
| 5 | Hold | 6 | −20° C. | 150 |
| 6 | Ramp | 1 | −15° C. | 150 |
| 7 | Hold | 20 | −15° C. | 150 |
| 8 | Ramp | 0.5 | −12° C. | 150 |
| 9 | Hold | 15.5 | −12 C. | 150 |
| 10 | Ramp | 15 | 35 C. | 50 |
| 11 | Hold | 10 | 35° C. | 50 |
| 12 | Ramp | 1 | 40 C. | 50 |
|  | Hold | 5 | 40 C. | 50 |
| Total |  | 89.25 | — | — |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, it will be apparent that certain solvents which are both chemically and physiologically related to the solvents disclosed herein may be substituted for the solvents described herein while the same or similar results would be achieved. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A stable lyophilized preparation comprising bendamustine hydrochloride, mannitol, and a trace amount of tertiary-butyl alcohol (TBA), wherein the ratio by weight of bendamustine hydrochloride to mannitol is 15:25.5.

2. The stable lyophilized preparation of claim 1 in a vial containing 25 mg bendamustine hydrochloride.

3. The stable lyophilized preparation of claim 1 in a vial containing 100 mg bendamustine hydrochloride.

4. A stable lyophilized preparation comprising bendamustine hydrochloride and mannitol in a ratio by weight of about 15:25.5, wherein the preparation is obtained by a process comprising:
   a) preparing a composition comprising bendamustine hydrochloride, mannitol, tertiary-butyl alcohol and water, wherein the bendamustine hydrochloride and mannitol are present in the ratio by weight of about 15:25.5, and
   b) lyophilizing the composition from step a) to obtain the preparation.

* * * * *